(12) United States Patent
Tateishi et al.

(10) Patent No.: US 8,080,067 B2
(45) Date of Patent: Dec. 20, 2011

(54) AZO PIGMENT COMPOSITION, PRODUCTION PROCESS OF AZO PIGMENT COMPOSITION, DISPERSION CONTAINING AZO PIGMENT COMPOSITION, COLORING COMPOSITION AND INK FOR INKJET RECORDING

(75) Inventors: Keiichi Tateishi, Shizuoka (JP); Shinya Hayashi, Shizuoka (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/921,365

(22) PCT Filed: Mar. 5, 2009

(86) PCT No.: PCT/JP2009/054180
§ 371 (c)(1),
(2), (4) Date: Sep. 7, 2010

(87) PCT Pub. No.: WO2009/110557
PCT Pub. Date: Sep. 11, 2009

(65) Prior Publication Data
US 2011/0017099 A1    Jan. 27, 2011

(30) Foreign Application Priority Data

Mar. 7, 2008  (JP) ................................. 2008-058711
Jun. 27, 2008  (JP) ................................. 2008-169182
Sep. 29, 2008  (JP) ................................. 2008-251879

(51) Int. Cl.
*A61Q 5/10* (2006.01)
*C09D 11/00* (2006.01)

(52) U.S. Cl. ...... 8/637.1; 8/639; 8/690; 8/692; 106/31.6

(58) Field of Classification Search .................. 8/637.1, 8/639, 690, 692; 106/31.6
See application file for complete search history.

(56) References Cited

U.S. PATENT DOCUMENTS 2,936,306 A    5/1960   Schmid et al.
(Continued)

FOREIGN PATENT DOCUMENTS

EP    1847570 A1    10/2007
(Continued)

OTHER PUBLICATIONS

STIC Search Report dated Jun. 8, 2011.*
(Continued)

*Primary Examiner* — Eisa Elhilo
(74) *Attorney, Agent, or Firm* — Sughrue Mion, PLLC

(57) ABSTRACT

To provide an azo pigment composition exhibiting very good hue and light fastness and having excellent tinctorial strength (color density) and preferably further provide an azo pigment composition containing an azo pigment having characteristic X-ray diffraction peaks at different positions or a tautomer thereof. An azo pigment composition comprising at least one kind of an azo pigment represented by formula (1) having characteristic X-ray diffraction peaks at Bragg angles (2θ±0.2°) of 7.6°, 25.6° and 27.7° in the CuKα characteristic X-ray diffraction or a tautomer thereof:

Formula (I):

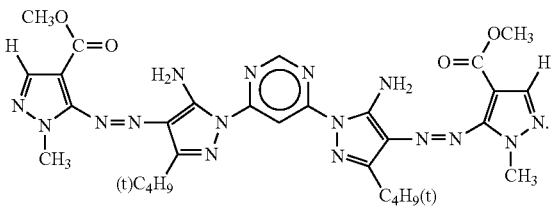

14 Claims, 2 Drawing Sheets

U.S. PATENT DOCUMENTS

| | | | |
|---|---|---|---|
| 4,282,144 A | 8/1981 | Weaver et al. | |
| 4,579,949 A | 4/1986 | Rochat et al. | |
| 4,870,164 A | 9/1989 | Kuhne et al. | |
| 5,194,088 A | 3/1993 | Babler et al. | |
| 2006/0107868 A1 | 5/2006 | Potenza et al. | |
| 2008/0058531 A1 | 3/2008 | Schmidt et al. | |
| 2008/0274283 A1* | 11/2008 | Tateishi et al. | 427/256 |

FOREIGN PATENT DOCUMENTS

| | | |
|---|---|---|
| EP | 1889881 A2 | 2/2008 |
| JP | 55-161856 A | 12/1980 |
| JP | 56-038354 A | 4/1981 |
| JP | 58-210084 A | 12/1983 |
| JP | 05-222314 A | 8/1993 |
| JP | 08-048908 A | 2/1996 |
| JP | 11-100519 A | 4/1999 |
| JP | 2002-371214 A | 12/2002 |
| JP | 2003-246942 A | 9/2003 |
| JP | 2003-277662 A | 10/2003 |
| JP | 2004-137487 A | 5/2004 |
| JP | 2005-213357 A | 8/2005 |
| JP | 2006-057076 A | 3/2006 |
| JP | 2007-063520 A | 3/2007 |
| JP | 2007-217681 A | 8/2007 |
| JP | 2007-302810 A | 11/2007 |
| WO | 2006/119846 A2 | 11/2006 |

OTHER PUBLICATIONS

International Search Report (PCT/ISA/210), for PCT/JP2009/054180, dated Apr. 28, 2009.

Written Opinion of the International Search Authority (PCT/ISA/237), for PCT/JP2009/054180, dated Apr. 28, 2009.

Extended European Search Report issued on Jun. 29, 2011 in corresponding European Patent Application No. 09717330.6.

* cited by examiner

AZO PIGMENT COMPOSITION, PRODUCTION PROCESS OF AZO PIGMENT COMPOSITION, DISPERSION CONTAINING AZO PIGMENT COMPOSITION, COLORING COMPOSITION AND INK FOR INKJET RECORDING

TECHNICAL FIELD

The present invention relates to an azo pigment composition, a production process of an azo pigment composition, a dispersion containing an azo pigment composition, a coloring composition and an ink for inkjet recording.

BACKGROUND ART

In recent years, a material for forming particularly a color image is predominating as an image recording material. Specifically, an inkjet recording material, a heat-sensitive transfer recording material, an electrophotographic recording material, a transfer silver halide light-sensitive material, a printing ink, a recording pen and the like are popularly used. Also, a color filter for recording and reproducing a color image is used, in the case of the filming equipment, in an imaging device such as CCD and, in the case of the display, in LCD or PDP. In these color image recording materials and color filters, colorants (dyes or pigments) of three primary colors by a so-called additive or subtractive color mixing method are used for displaying or recording a full color image, but a colorant having absorption characteristics capable of realizing a preferred color reproduction region and having fastness high enough to endure various use conditions and environmental conditions is not found at present, and improvements are keenly demanded.

The dyes and pigments used in the above-described applications are commonly required to have the following properties. For example, it is required to have good absorption characteristics in terms of color reproduction and show good fastness to usage environment conditions, such as light fastness, heat resistance and resistance to an oxidative gas such as ozone. In addition, in the case where the colorant is a pigment, the requisite properties further include, for example, being substantially insoluble in water or an organic solvent, showing good chemical resistance, and not impairing the preferred absorption characteristics in the molecular dispersion state even when used as a particle. These requisite characteristics can be controlled by the degree of the intermolecular interaction, but absorption characteristics and fastness are in a trade-off relationship and therefore, it is difficult to satisfy both at the same time.

Moreover, in using a pigment, other than the properties described above, it is also required, for example, to have a particle size and a particle shape necessary for bringing out the desired transparency, to show good fastness to usage environment conditions, such as light fastness, heat resistance, resistance to an oxidative gas (e.g., ozone), and chemical resistance to an organic solvent, a sulfurous acid gas or the like, and to be capable of dispersing even into a microparticle in the medium used and keeping stable the dispersed state. Above all, a pigment having good hue and being fast to light, wet heat and environmental active gases, in particular, a pigment having high tinctorial strength and being fast to light, is strongly demanded.

More specifically, the performance required of the pigment is diversified as compared with the dye that is required to have performances as a colorant molecule, and not only performances as a colorant molecule but also all of the above-described requisite performances as a solid (fine particle dispersion) resulting from aggregation of colorant molecules must be satisfied. In turn, the compound group usable as a pigment is extremely limited as compared with the dye and even when a pigment is derived from a high-performance dye, the pigment capable of satisfying the requisite performances as a fine particle dispersion is very few in number and cannot be easily developed. This can be confirmed also by the fact that the number of pigments registered in the Color Index is less than 1/10 of the number of dyes.

Azo pigments are widely used in a printing ink, an inkjet ink, an electrophotographic material and the like because of their excellent coloristic characteristics, i.e., hue and tinctorial strength. Of these azo dyes, a yellow diarylide pigment and a red naphthol azo pigment are most typically used. Examples of the diarylide pigment include C.I. Pigment Yellow 12, C.I. Pigment Yellow 13 and C.I. Pigment Yellow 17, and examples of the naphthol azo pigment include C.I. Pigment Red 208 and C.I. Pigment Red 242. However, these pigments are very poor in the fastness, particularly light fastness, and when the printed material is exposed to light, the pigment is decomposed to cause fading. Thus, these are not suitable for storage of the printed material for a long period of time.

In order to overcome such a defect, an azo pigment improved in the fastness by increasing the molecular weight or introducing a group having strong intermolecular interaction is disclosed (see, for example, Patent Documents 1 to 3). However, even the improved pigment is still insufficient, though the light fastness of the pigment described, for example, in Patent Document 1 is improved. Also, the pigments described, for example, in Patent Documents 2 to 3 bring about green tinting in the hue and decrease in the tinctorial strength and disadvantageously suffer from poor coloristic characteristics.

In Patent Documents 4 and 5, colorants having excellent absorption characteristics for color reproduction and sufficiently high fastness are disclosed. However, all of specific compounds described in these patent documents dissolve in water or an organic solvent and are insufficient in the chemical resistance.

In the case of producing a full color by a subtractive color mixing method using three colors of yellow, magenta and cyan or four colors with the addition of black, when a pigment poor in the fastness is used as the pigment for one color, the gray balance of the printed material is changed with the passage of time, and when a pigment poor in the coloristic characteristics is used, the color reproducibility at the printing is decreased. Accordingly, for obtaining a printed material capable of maintaining high color reproducibility for a long period of time, a pigment or pigment dispersion satisfying both coloristic characteristics and fastness is demanded.

Many of azo colorants have various visible light absorptions and therefore, have been conventionally utilized as a colorant in various fields. The azo colorant is being used in various fields, for example, for coloring a synthetic resin, as a colorant for printing ink or sublimation-type heat-sensitive transfer material, or as a colorant for inkjet ink or color filter. The major performance as a colorant, which is required of an azo colorant, includes an absorption spectrum. The hue of a colorant greatly affects the color tone, touch and the like of an article colored with the colorant and gives a great effect on the visual perception. Therefore, studies have been long made on the absorption spectrum of colorant.

A conventionally known azo dye using a nitrogen-containing 5-membered ring as the azo component is disclosed also in Patent Documents 6 and 7.

On the other hand, many of representative organic pigments have polymorphs, and such a pigment is known to take two or more crystal morphologies, despite the same chemical composition.

Some organic pigments can be obtained, like an azo pigment, as fine and size-regulated particles by selecting appropriate reaction conditions at the synthesis, some can be obtained, like a copper phthalocyanine green pigment, as a pigment after very fine aggregated particles produced at the synthesis are subjected to particle growth and size regulation in the post-process, and some can be obtained, like a copper phthalocyanine blue pigment, as a pigment after coarse irregular particles produced at the synthesis are subjected to pulverization and size regulation in the post-process. For example, a diketopyrrolopyrrole pigment is generally synthesized by reacting a succinic acid diester and an aromatic nitrile in an organic solvent (see, for example, Patent Document 8). The crude diketopyrrolopyrrole pigment is heat-treated in water or an organic solvent and then subjected to disintegration such as wet grinding, whereby the pigment is obtained in the form suitable for use (see, for example, Patent Document 9). For example, C.I. Pigment Red 254 that is a diketopyrrolopyrrole pigment is known to have α-type and β-type crystal morphologies (see, for example, Patent Document 10). Also, C.I. Pigment Yellow 181 that is an azo pigment is known to have several kinds of crystal morphologies (see, for example, Patent Document 11).

Patent Document 1: JP-A-56-38354 (the term "JP-A" as used herein means an "unexamined published Japanese patent application")
Patent Document 2: U.S. Pat. No. 2,936,306
Patent Document 3: JP-A-11-100519
Patent Document 4: JP-A-2005-213357
Patent Document 5: JP-A-2003-246942
Patent Document 6: JP-A-55-161856
Patent Document 7: JP-A-2002-371214
Patent Document 8: JP-A-58-210084
Patent Document 9: JP-A-5-222314
Patent Document 10: JP-A-8-48908
Patent Document 11: U.S. Patent Application Publication 2008/058531, specification

DISCLOSURE OF THE INVENTION

Problems that the Invention is to Solve

The present invention relates to an azo pigment composition comprising an azo pigment that is a crystal form of bisazo pigment where a pyrazole ring having a specific substituent and a colorant mother nucleus composed of an azo group and another pyrazole ring differing in the substituent are connected through a pyrimidine ring, or its tautomer. Excellent stability and production process thereof have been heretofore not known.

An object of the present invention is to provide an azo pigment composition exhibiting very good hue and light fastness and having excellent tinctorial strength (color density) and preferably further provide an azo pigment composition containing an azo pigment having characteristic X-ray diffraction peaks at different positions or a tautomer thereof.

Another object of the present invention is to provide a coloring composition comprising the azo pigment composition.

Still another object of the present invention is to provide a production process of the azo pigment composition, which can efficiently produce the azo pigment composition with good reproducibility while controlling the specific structural isomerism and crystalline polymorphism.

Also, an object of the present invention is to provide a coloring composition and an ink for inkjet recording, each comprising a dispersion of the azo pigment composition.

Means for Solving the Problems

Under these circumstances, the present inventors have made intensive studies, as a result, it has been found that an azo pigment composition comprising an azo pigment having characteristic X-ray diffraction peaks at specific positions or a tautomer thereof exhibits very good dispersibility and dispersion stability and has excellent hue and tinctorial strength.

Also, it has been found that a dispersion and a coloring composition, each having dispersed therein the azo pigment composition, can produce an ink for inkjet recording having excellent hue and tinctorial strength. Furthermore, a production process of the azo pigment composition, which can efficiently produce the azo pigment composition with good reproducibility while controlling the specific structural isomerism and crystalline polymorphism, has been found. The present invention has been accomplished based on these findings.

That is, the present invention includes the followings.

[1] An azo pigment composition containing at least one kind of an azo pigment represented by formula (1) having characteristic X-ray diffraction peaks at Bragg angles) (2θ±0.2°) of 7.6°, 25.6° and 27.7° in the CuKα characteristic X-ray diffraction or a tautomer thereof:

[Chem. 1]

Formula (1):

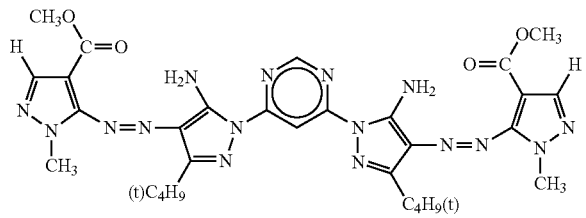

[2] The azo pigment composition as described in [1], wherein the composition further comprises at least from 0 to 50 mass % of an azo pigment represented by formula (1) with a crystal morphology having characteristic X-ray diffraction peaks at Bragg angles (2θ±0.2°) of 7.0°, 26.4° and 27.3° in the CuKα characteristic X-ray diffraction or a tautomer thereof.

[3] The azo pigment composition as described in [2], wherein the azo pigment represented by formula (1) with a crystal morphology having characteristic X-ray diffraction peaks at Bragg angles (2θ±0.2°) of 7.0°, 26.4° and 27.3° in the CuKα characteristic X-ray diffraction or a tautomer thereof is contained in an amount of at least from 0 to 20 mass %.

[4] The azo pigment composition as described in [2] or [3], wherein the azo pigment represented by formula (1) with a crystal morphology having characteristic X-ray diffraction peaks at Bragg angles (2θ±0.2°) of 7.0°, 26.4° and 27.3° in the CuKα characteristic X-ray diffraction or a tautomer thereof is contained in an amount of at least from 0 to 10 mass %.

[5] The azo pigment composition as described in any one of [1] to [4], wherein the composition further comprises at least from 0 to 50 mass % of an azo pigment represented by formula (1) with a crystal morphology having characteristic X-ray diffraction peaks at Bragg angles (2θ±0.2) of 6.4°, 26.4° and 27.2° in the CuKα characteristic X-ray diffraction or a tautomer thereof.

[6] The azo pigment composition as described in [5], wherein the azo pigment represented by formula (1) with a crystal morphology having characteristic X-ray diffraction peaks at Bragg angles (2θ±0.2°) of 6.4°, 26.4° and 27.2° in the CuKα characteristic X-ray diffraction or a tautomer thereof is contained in an amount of at least from 0 to 20 mass %.

[7] The azo pigment composition as described in [5] or [6], wherein the azo pigment represented by formula (1) with a crystal morphology having characteristic X-ray diffraction peaks at Bragg angles (2θ±0.2°) of 6.4°, 26.4° and 27.2° in the CuKα characteristic X-ray diffraction or a tautomer thereof is contained in an amount of at least from 0 to 10 mass %.

[8] A process for producing an azo pigment composition comprising at least one kind of an azo pigment represented by the following formula (1) or a tautomer thereof, comprising a step of performing an azo coupling reaction between a diazonium salt derived from a heterocyclic amine represented by the following formula (2) and a compound represented by the following formula (3):

[Chem. 2]

Formula (2):

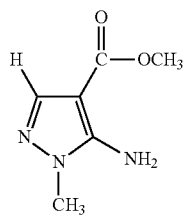

Formula (3):

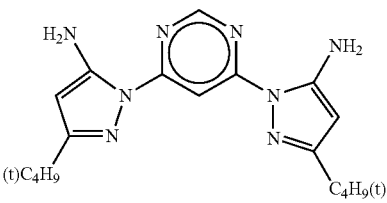

Formula (1):

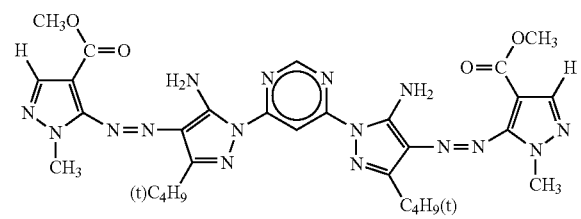

[9] The production process as described in [8], which further comprises a step of performing a post-treatment.
[10] An azo pigment composition produced by the production process described in [8] or [9].
[11] A dispersion comprising the azo pigment composition described in any one of [1] to [7] and [10].
[12] The pigment dispersion as described in [11], wherein the volume average particle diameter is from 0.01 to 0.25 μm.
[13] A coloring composition comprising the azo pigment composition described in any one of [1] to [7] and [10] as a coloring agent.
[14] An ink for inkjet recording comprising the azo pigment composition described in any one of [1] to [7] and [10] as a coloring agent.

Advantage of the Invention

According to the present invention, an azo pigment excellent in coloristic characteristics such as tinctorial strength and hue and also excellent in the dispersibility and dispersion stability is provided. By dispersing the pigment of the present invention in various mediums, a pigment dispersion excellent in coloristic characteristics, dispersibility and dispersion stability is provided. The pigment dispersion can be used as a coloring material with excellent light fastness, for example, in an ink for printing such as inkjet recording, a color toner for electrophotography, a color filter for a display such as LCD and PDP or an imaging device such as CCD, a coating material, and a colored plastic.

BEST MODE FOR CARRYING OUT THE INVENTION

Figure 1:
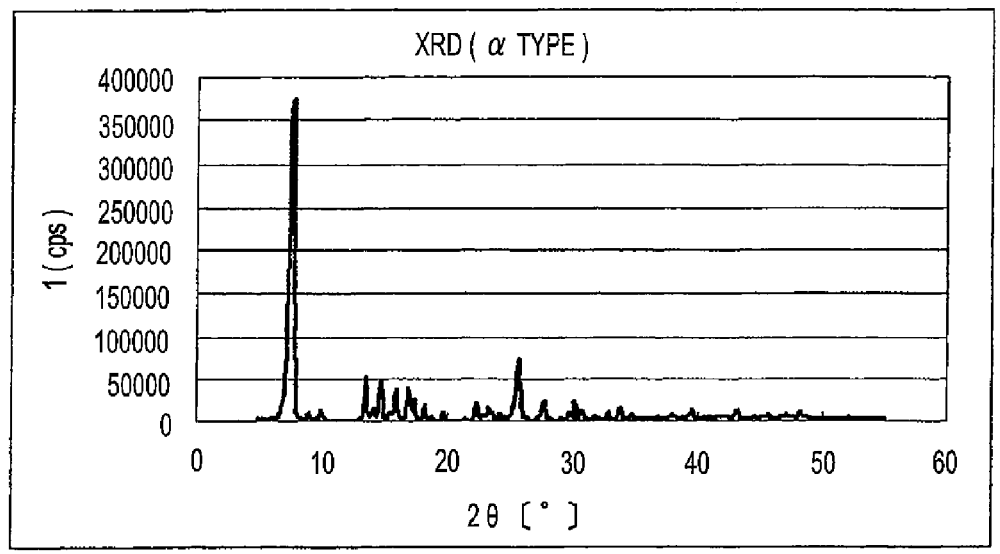
FIG. 1 A view showing the X-ray diffraction of Azo Pigment Composition 1 of α-type crystal morphology synthesized in accordance with Synthesis Example 1.

The present invention is described in detail below.

The azo pigment composition of the present invention contains at least one kind of an azo pigment represented by formula (1) with a crystal morphology having characteristic X-ray diffraction peaks at Bragg angles (2θ±0.2°) of 7.6°, 25.6° and 27.7° in the CuKα characteristic X-ray diffraction or a tautomer thereof.

In the present invention, hereinafter, the azo pigment represented by formula (1) having characteristic X-ray diffraction peaks at Bragg angles (2θ±0.2°) of 7.6°, 25.6° and 27.7° in the CuKα characteristic X-ray diffraction is referred to as an α-type crystal morphology azo pigment.

Also, in the present invention, the azo pigment represented by formula (1) having characteristic X-ray diffraction peaks at Bragg angles (2θ±0.2°) of 7.0°, 26.4° and 27.3° in the CuKα characteristic X-ray diffraction is referred to as a β-type crystal morphology azo pigment.

Furthermore, in the present invention, the azo pigment represented by formula (1) having characteristic X-ray diffraction peaks at Bragg angles (2θ±0.2°) of 6.4°, 26.4° and 27.2° in the CuKα characteristic X-ray diffraction is referred to as a γ-type crystal morphology azo pigment.

Formula (I):

[Chem. 3]

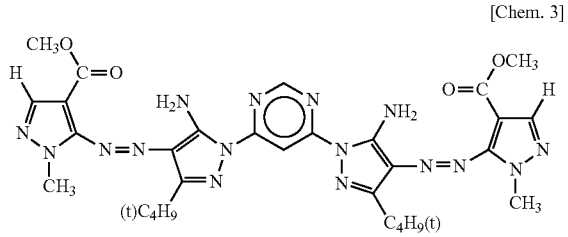

In the present invention, with respect to the method for measuring the content of the azo pigment composition containing a β-type crystal morphology azo pigment in the α-type crystal morphology azo pigment represented by formula (1) or the content of the azo pigment composition containing a γ-type crystal morphology azo pigment in the α-type crystal morphology azo pigment represented by formula (1), for example, the content can be easily calculated from the ratio of intensity to each of the peak at Bragg angle (2θ±0.2°) of 7.6°, the peak at Bragg angle (2θ±0.2°) of 7.0° and the peak at Bragg angles (2θ±0.2°) of 6.4° in the CuKα characteristic X-ray diffraction based on measurement results of X-ray diffraction using a sample in which respective azo pigments of α-type crystal morphology, β-type crystal morphology and γ-type crystal morphology as authentic preparations are mixed by arbitrarily changing the mass ratio. The X-ray diffraction measurement of the present invention was performed in accordance with Japanese Industrial Standards JIS K0131 (General Rule of X-ray Diffraction Analysis) in a powder X-ray diffraction measuring apparatus, RINT2500 (manufactured by Rigaku Corporation).

In the present invention, the method for obtaining an azo pigment containing a β-type crystal morphology azo pigment or a γ-type crystal morphology azo pigment includes a method of controlling the reaction conditions (e.g., solvent species, pH value, reaction temperature, reaction time) in the step of performing an azo coupling reaction between a diazonium salt derived from the heterocyclic amine represented by formula (2) and a compound represented by formula (3). Furthermore, the pigment can be easily obtained by controlling the conditions (e.g., solvent species, pH value, reaction temperature, reaction time) when the azo pigment obtained in the step above is further treated in a post-process.

In the azo pigment composition of the present invention, the α-type crystal morphology azo pigment, the β-type crystal morphology azo pigment and the γ-type crystal morphology azo pigment may be separately produced and mixed in an arbitrary preferred content ratio before use. As for another production process, an azo pigment composition produced directly in a preferred mixing composition ratio at the production by controlling the above-described reaction conditions during the production of the azo pigment composition may be used.

In the case of a single crystal morphology, the molecules exist densely and the intermolecular interaction is strengthened, as a result, the solvent resistance, thermal stability, light fastness, gas resistance and printing density are increased and the color reproduction region is widened. Accordingly, the α-type crystal morphology azo pigment is preferably a crystal morphology having characteristic X-ray diffraction peaks at Bragg angles (2θ±0.2°) of 7.6° and 25.6° in the CuKα characteristic X-ray diffraction, more preferably a crystal morphology having characteristic X-ray diffraction peaks at 7.6°, 13.5°, 25.6° and 27.7°. Above all, a crystal morphology having characteristic X-ray diffraction peaks at 7.6°, 13.5°, 15.9°, 16.9°, 25.6° and 27.7° is most preferred.

In the azo pigment composition of the present invention, assuming that the height of the peak at a Bragg angles (2θ±0.2°) of 7.6° in the CuKα characteristic X-ray diffraction is 1, the height of the peak at 7.0° is preferably 0.00001 or more in view of sharp particle size distribution of the pigment dispersion. Also, the height of the peak at 6.4° is preferably 0.2 or less, because from the standpoint of hue, an excess increase of red tint is prevented and this is preferred in terms of color reproducibility. Therefore, assuming that the height of the peak at a Bragg angles (2θ±0.2°) of 7.6° in the CuKα characteristic X-ray diffraction is 1, the height of the peak at 7.0° is preferably from 0.00001 to 0.2, more preferably from 0.0001 to 0.1, and most preferably from 0.0001 to 0.05.

The azo pigment composition preferably contains an azo pigment represented by formula (1) with a crystal morphology having characteristic X-ray diffraction peaks at Bragg angles (2θ±0.2°) of 7.0°, 26.4° and 27.3° in the CuKα characteristic X-ray diffraction (β-type crystal morphology azo pigment) or a tautomer thereof in an amount of at least from 0 to 50 mass %, more preferably from 0 to 20 mass %, still more preferably from 0 to 10 mass %.

The azo pigment composition preferably contains the β-type crystal morphology azo pigment in the range above, because when the azo pigment composition is used for a dispersion, a coloring composition, an ink for inkjet recording or the like, an excellent effect can be obtained on the control of particle size distribution of the pigment dispersion (for example, the control of liquid properties of the pigment ink).

In the azo pigment composition of the present invention, assuming that the height of the peak at a Bragg angles (2θ±0.2°) of 7.6° in the CuKα characteristic X-ray diffraction is 1, when the height of the peak at 6.4° is 0.00001 or more, a red tint is increased in green-tinted yellow from the standpoint of hue and this is preferred in view of tinctorial strength. Also, the height of the peak at 6.4° is preferably 0.2 or less, because from the standpoint of hue, an excess increase of red tint is prevented and this is preferred in terms of color reproducibility. Therefore, assuming that the height of the peak at a Bragg angles (2θ±0.2°) of 7.6° in the CuKα characteristic X-ray diffraction is 1, the height of the peak at 6.4° is preferably from 0.00001 to 0.2, more preferably from 0.0001 to 0.1, and most preferably from 0.0001 to 0.05.

The azo pigment composition preferably contains an azo pigment represented by formula (1) with a crystal morphology having characteristic X-ray diffraction peaks at Bragg angles (2θ±0.2°) of 6.4°, 26.4° and 27.2° in the CuKα characteristic X-ray diffraction (γ-type crystal morphology azo pigment) or a tautomer thereof in an amount of at least from 0 to 50 mass %, more preferably from 0 to 20 mass %, still more preferably from 0 to 10 mass %.

The azo pigment composition preferably contains the γ-type crystal morphology azo pigment in the range above, because when the azo pigment composition is used for a dispersion, a coloring composition, an ink for inkjet recording or the like, excellent performance to impart high hue and high tinctorial strength can be brought out.

The primary particle of the azo pigment composition represented by formula (1) preferably has, as observed by a transmission microscope, a length in the long axis direction of 0.01 to 30 μm, more preferably from 0.02 to 15 μm, still more preferably from 0.03 to 1 μm.

If the length in the long axis direction of the primary particle when observed by a transmission microscope is 0.01 μm or less, fastness to light or ozone may significantly decrease, the particle may have difficult dispersibility because of its propensity for aggregation, or the stability of the pigment dispersion may deteriorate, whereas if it is 30 μm or more, the particle dispersed into a desired volume average particle diameter enters an overdispersion state (a morphology where primary particles are broken) and allows the pigment particle surface to expose an active face, as a result, aggregation and precipitation may readily occur and the storage stability of the pigment dispersion may significantly decrease.

By controlling the primary particle size to fall in the range above, strong intramolecular/intermolecular interaction is allowed to take place, resulting in pigment particles forming a firm, stable three-dimensional network, and this advantageously enables the pigment particle to exhibit high fastness to light, heat, humidity and oxidative gas and ensures excellent storage stability of a coloring material using the pigment dispersion.

In measuring the volume average particle diameter of the pigment dispersion containing the pigment composition of the present invention, a Nanotrac UPA particle size distribution analyzer (UPA-EX150, manufactured by Nikkiso Co., Ltd.) was used. The measurement was performed according to a predetermined measurement method after placing 3 ml of the pigment dispersion in the measurement cell. In this connection, as for the parameter input at the measurement, the ink viscosity was used for the viscosity, and the pigment density was used for the density of dispersed particles.

The average particle diameter of the α-type crystal morphology azo pigment represented by formula (1) is preferably from 0.01 to 30 μm, more preferably from 0.02 to 10 μm, and most preferably from 0.03 to 1 μm.

The average particle diameter in the range above is preferred, because the density of the printed matter is thick, the stability of the dispersion is increased, color reproducibility of a mixed color part of red, green and the like is enhanced, the transparency is high, and at the printing by an inkjet system or the like, clogging of a nozzle hardly occurs. Also, conversely, difficult occurrence of aggregation and high aging stability of the dispersion are brought about, and this is preferred.

The volume average particle diameter of the pigment dispersion containing the pigment composition of the present invention can be easily adjusted to the range above by appropriately combining later-described pigment dispersion conditions.

The process for producing an azo pigment composition containing at least one kind of an azo pigment represented by formula (1) or a tautomer thereof is described in detail below.

The production process of the azo pigment composition comprises a step of performing an azo coupling reaction between a diazonium salt derived from a heterocyclic amine represented by the following formula (2) and a compound represented by the following formula (3):

[Chem. 4]

Formula (2):

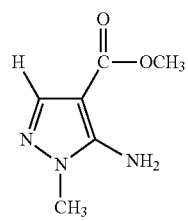

Formula (3):

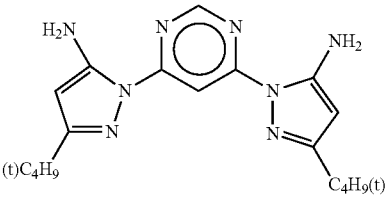

Formula (I):

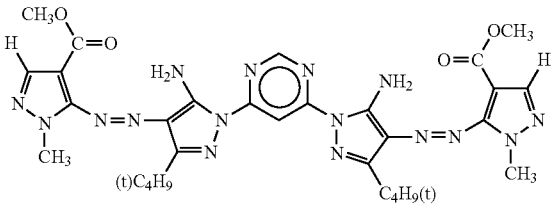

[Step of Preparing Diazonium Salt of Heterocyclic Amine]

The preparation of a diazonium salt and the coupling reaction between the diazonium salt and a compound represented by formula (3) can be performed by conventional methods.

For the preparation of a diazonium salt of a heterocyclic amine represented by formula (2), a conventional method for preparing a diazonium salt by using a nitrosonium ion source, for example, nitrous acid, nitrite or nitrosylsulfuric acid, in a reaction medium containing an acid (e.g., hydrochloric acid, sulfuric acid, phosphoric acid, acetic acid, propionic acid, methanesulfonic acid, trifluoromethanesulfonic acid) can be applied.

Preferred examples of the acid include a case of using acetic acid, propionic acid, methanesulfonic acid, phosphoric acid and sulfonic acid individually or in combination. Above all, a combination use of phosphoric acid or acetic acid and sulfuric acid, a combination use of acetic acid and propionic acid, and a combination use of acetic acid, propionic acid and sulfuric acid are more preferred, and a combination use of acetic acid and propionic acid, and a combination use of acetic acid, propionic acid and sulfuric acid are still more preferred.

As for preferred examples of the reaction medium (solvent), an organic acid and an inorganic acid are preferably used. In particular, phosphoric acid, sulfuric acid, acetic acid, propionic acid and methane sulfonic acid are more preferred, and acetic acid and/or propionic acid are still more preferred.

Preferred examples of the nitrosonium ion source include nitrous acid esters, nitrites and nitrosylsulfuric acid. Among these, sodium nitrite, potassium nitrite, isoamyl nitrite and nitrosylsulfuric acid (for example, an ONHSO$_4$ sulfuric acid solution) are more preferred, and isoamyl nitrite and nitrosylsulfuric acid (for example, a 40 to 50 mass % ONHSO$_4$ sulfuric acid solution) are still more preferred. Above all, a diazonium salt can be stably and efficiently prepared by using nitrosylsulfuric acid in the above-described preferred acid-containing reaction medium.

The amount of the solvent used is preferably from 0.5 to 50 times by mass, more preferably from 1 to 20 times by mass, still more preferably from 3 to 15 times by mass, based on the diazonium component of formula (2).

In the present invention, the diazo component of formula (2) may be either in a state of being dispersed in a solvent or depending on the kind of the diazo component, in a solution state.

The amount of the nitrosonium ion source used is preferably from 0.95 to 5.0 equivalents, more preferably from 1.00 to 3.00 equivalents, still more preferably from 1.00 to 1.10 equivalents, based on the diazo component.

The reaction temperature is preferably from −15° C. to 40° C., more preferably from −5° C. to 35° C., still more preferably from −0° C. to 30° C. If the reaction temperature is less than −10° C., the reaction rate becomes extremely slow and the synthesis takes an unprofitably long time, whereas synthesis at a high temperature exceeding 40° C. involves an increase in the production of by-products and this is not preferred.

The reaction time is preferably from 30 to 300 minutes, more preferably from 30 to 200 minutes, still more preferably from 30 to 150 minutes.

[Coupling Reaction Step]

The coupling reaction step can be performed in a reaction medium of from acidic to basic but in the case of the azo pigment of the present invention, is preferably performed in a reaction medium of from acidic to neutral, more preferably in an acidic reaction medium, because decomposition of the diazonium salt can be suppressed and an azo pigment can be efficiently derived.

As for the preferred examples of the reaction medium (solvent), an organic acid, an inorganic acid and an organic solvent may be used, but an organic solvent is particularly preferred, and a solvent causing no liquid separation phenomenon during reaction and providing a uniform solution with the solvent is preferred. Examples thereof include an alcoholic organic solvent such as methanol, ethanol, propanol, isopropanol, butanol, tert-butyl alcohol and amyl alcohol, a ketone-based organic solvent such as acetone and methyl ethyl ketone, a diol-based organic solvent such as ethylene glycol, diethylene glycol, triethylene glycol, propylene glycol, dipropylene glycol and 1,3-propanediol, an ether-based organic solvent such as ethylene glycol monomethyl ether, ethylene glycol monoethyl ether and ethylene glycol diethyl ether, tetrahydrofuran, dioxane and acetonitrile. The solvent may be a mixed solution of two or more kinds of these solvents.

An organic solvent having a polarity parameter (ET) value of 40 or less is preferred. Above all, a glycol-based solvent having two or more hydroxyl groups in the solvent molecule, an alcohol-based solvent having a carbon number of 3 or less, and a ketone-based solvent having a total carbon number of 5 or less are preferred, and an alcohol solvent having a carbon number of 2 or less (e.g., methanol, ethylene glycol) and a ketone-based solvent having a total carbon number of 4 or less (e.g., acetone, methyl ethyl ketone) are more preferred. A mixed solvent of these is also included in the organic solvent above.

The amount of the solvent used is preferably from 1 to 100 times by mass, more preferably from 1 to 50 times by mass, still more preferably from 2 to 30 times by mass, based on the coupling component represented by formula (3).

In the present invention, the coupling component of formula (3) may be either in a state of being dispersed in a solvent or depending on the kind of the coupling component, in a solution state.

The amount of the coupling component used is, in terms of the diazo component per azo coupling site, preferably from 0.95 to 5.0 equivalents, more preferably from 1.00 to 3.00 equivalents, still more preferably from 1.00 to 1.50 equivalents.

The reaction temperature is preferably from −30° C. to 30° C., more preferably from −15° C. to 10° C., still more preferably from −10° C. to 5° C. If the reaction temperature is less than −30° C., the reaction rate becomes extremely slow and the synthesis takes an unprofitably long time, whereas synthesis at a high temperature exceeding 30° C. involves an increase in the production of by-products and this is not preferred.

The reaction time is preferably from 30 to 300 minutes, more preferably from 30 to 200 minutes, still more preferably from 30 to 150 minutes.

In the production process of an azo pigment composition of the present invention, the product (crude azo pigment) obtained by these reactions is usually treated according to a post-treatment method of normal organic synthesis reaction and then, with or without purification, can be used.

That is, for example, the product isolated from the reaction system can be used without purification or can be used after performing purification operations such as recrystallization and salt formation individually or in combination.

Also, when the reaction is completed, the reaction solvent may or may not be removed by distillation, the reaction solution may or may not be neutralized by pouring it in water or ice, and the product isolated or extracted with an organic solvent/aqueous solution may be used without purification or after performing purification operations such as recrystallization, crystallization and salt formation individually or in combination.

The production process of an azo pigment composition of the present invention is described in more detail.

The production process of an azo pigment composition of the present invention includes a coupling reaction between a diazonium compound obtained by diazonium formation of a heterocyclic amine represented by formula (2) and a compound represented by formula (3), wherein the coupling reaction is performed after the compound of formula (3) is dissolved in an organic solvent.

The reaction for diazonium formation of a heterocyclic amine represented by formula (2) can be performed, for example, by reacting the heterocyclic amine with a reagent such as sodium nitrite and nitrosylsulfuric acid in an acidic solvent such as sulfuric acid, phosphoric acid and acetic acid at a temperature of 15° C. or less for approximately from 10 minutes to 6 hours. The coupling reaction is preferably performed by reacting a diazonium salt obtained by the above-described method and a compound represented by formula (3) at 40° C. or less, preferably 15° C. for less, for approximately from 10 minutes to 12 hours.

The tautomerism and/or crystalline polymorphism described above can be controlled by the production conditions during the coupling reaction. As for the process of producing a pigment composition containing an α-type crystal as the main component, which is a more preferred embodiment of the present invention, for example, the process of the present invention where the coupling reaction is preformed after once dissolving the compound represented by formula (3) in an organic solvent is preferably used. Examples of the organic solvent which can be used here include an alcohol solvent and a ketone-based solvent. Preferred examples of the alcohol solvent include methanol, ethanol, isopropanol, ethylene glycol and diethylene glycol, with methanol being more preferred. Preferred examples of the ketone-based solvent include acetone, methyl ethyl ketone and cyclohexanone, with acetone being more preferred.

Another production process of an azo pigment composition of the present invention includes a coupling reaction between a diazonium compound obtained by diazonium formation of a heterocyclic amine represented by formula (2)

and a compound represented by formula (3), wherein the coupling reaction is performed in the presence of a polar aprotic solvent.

The pigment composition containing an α-type crystal as the main component can be efficiently produced also by the method of performing the coupling reaction in the presence of a polar aprotic solvent. Examples of the polar aprotic solvent include N,N-dimethylformamide, N,N-dimethylacetamide, N-methyl-2-pyrrolidone, dimethylsulfoxide, tetramethylurea, acetone, methyl ethyl ketone, acetonitrile and a mixed solvent thereof. Among these solvents, acetone, methyl ethyl ketone, N,N-dimethylacetamide and acetonitrile are preferred. In the case of using such a solvent, the compound of formula (3) may or may not be completely dissolved in the solvent.

According to the usage, the compound obtained by the above-described production process may or may not be subjected to a purification step of adjusting the pH by adding a base. In the case of adjusting the pH, the pH is preferably from 4 to 10. The pH is more preferably from 5 to 8, still more preferably from 5.5 to 7.5.

The pH is preferably 10 or less in view of hue because discoloration/color fading does not occur and a constant hue quality is ensured, and the pH is preferably 4 or more from the standpoint that when used as an ink for inkjet recording, a problem such as corrosion of a nozzle is hardly caused.

The compound represented by formula (1) is obtained as a crude azo pigment (crude) by the above-described production process.

The present invention also relates to an azo pigment composition produced by the production process above.

[Post-Treatment Step]

The production process of the present invention preferably includes a step of performing a post-treatment (finishing). The "finishing" as used in the present invention indicates a treatment for adjusting the crystal morphology, the particle size or shape, and the like. Examples of the method for this post-treatment step include a process of controlling the pigment particle by a milling treatment such as solvent salt milling, salt milling, dry milling, solvent milling and acid pasting or by a solvent heating treatment, and a process of treating the surface with a resin, a surfactant or a dispersant.

As for the post-treatment of the compound represented by formula (1) of the present invention, a solvent heating treatment and/or a solvent salt milling are preferably performed. For example, an α-type crystal morphology azo pigment can be produced by performing refluxing in an organic solvent from which water is removed.

Examples of the solvent used for the solvent heating treatment include water, an aromatic hydrocarbon-based solvent such as toluene and xylene, a halogenated hydrocarbon-based solvent such as chlorobenzene and o-dichlorobenzene, an alcohol-based solvent such as isopropanol and isobutanol, a polar aprotic organic solvent such as N,N-dimethylformamide, N,N-dimethylacetamide, N-methyl-2-pyrrolidone, acetone, methyl ethyl ketone and acetonitrile, glacial acetic acid, pyridine and a mixture thereof. In the solvent described above, an inorganic or organic acid or base may be further added. The temperature of the solvent heating treatment varies depending on the desired primary particle diameter of the pigment but is preferably from 40 to 150° C., more preferably from 60 to 100° C. Also, the treating time is preferably from 30 minutes to 24 hours.

In the solvent salt milling, for example, the crude azo pigment, an inorganic salt and an organic solvent incapable of dissolving these are charged into a kneading machine and kneading milling is performed therein. As for the inorganic salt, a water-soluble inorganic salt can be suitably used and, for example, an inorganic salt such as sodium chloride, potassium chloride and sodium sulfate is preferably used. Use of an inorganic salt having an average particle diameter of 0.5 to 50 μm is more preferred. The amount of the inorganic salt used is preferably from 3 to 20 times by mass, more preferably from 5 to 15 times by mass, based on the crude azo pigment. As for the organic solvent, a water-soluble organic solvent can be suitably used and in view of safety, a high boiling point solvent is preferred, because the solvent enters an evaporable state due to rise in the temperature during kneading. Examples of such an organic solvent include diethylene glycol, glycerin, ethylene glycol, propylene glycol, liquid polyethylene glycol, liquid polypropylene glycol, 2-(methoxymethoxy)ethanol, 2-butoxyethanol, 2-(isopentyloxy)ethanol, 2-(hexyloxy)ethanol, diethylene glycol monomethyl ether, diethylene glycol monoethyl ether, diethylene glycol monobutyl ether, triethylene glycol, triethylene glycol monomethyl ether, 1-methoxy-2-propanol, 1-ethoxy-2-propanol, dipropylene glycol, dipropylene glycol monomethyl ether, dipropylene glycol monomethyl ether, dipropylene glycol, and a mixture thereof. The amount of the water-soluble organic solvent used is preferably from 0.1 to 5 times by mass based on the crude azo pigment. The kneading temperature is preferably from 20 to 130° C., more preferably from 40 to 110° C. Examples of the kneading machine which can be used include a kneader and a mix-muller.

[Pigment Dispersion]

The pigment dispersion of the present invention contains at least one kind of the azo pigment of the present invention. Thanks to this configuration, the pigment dispersion can be a pigment dispersion excellent in the coloristic characteristics, durability and dispersion stability.

The pigment dispersion of the present invention may be aqueous or non-aqueous but is preferably an aqueous pigment dispersion. In the aqueous pigment dispersion of the present invention, the aqueous liquid used for dispersing the pigment therein may be a mixture of water as the main component and a hydrophilic organic solvent added, if desired. Examples of the hydrophilic organic solvent include alcohols such as methanol, ethanol, propanol, isopropanol, butanol, isobutanol, sec-butanol, tert-butanol, pentanol, hexanol, cyclohexanol and benzyl alcohol, polyhydric alcohols such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol and thiodiglycol, glycol derivatives such as ethylene glycol monomethyl ether, ethylene glycol monoethyl ether, ethylene glycol monobutyl ether, diethylene glycol monomethyl ether, diethylene glycol monobutyl ether, diethylene glycol monomethyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate triethylene glycol monoethyl ether and ethylene glycol monophenyl ether, amines such as ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine and tetramethylpropylenediamine, formamide, N,N-dimethylformamide, N,N-dimethylacetamide, dimethylsulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile and acetone.

Moreover, the aqueous pigment dispersion of the present invention may contain an aqueous resin. The aqueous resin includes a water-soluble resin capable of dissolving in water, a water-dispersible resin capable of dispersing in water, a colloidal dispersion resin, and a mixture thereof. Specific examples of the aqueous resin include acryl-based, styrene-acryl-based, polyester-based, polyamide-based, polyurethane-based and fluorine-based resins.

Moreover, for enhancing the dispersion of the pigment and the quality of the image, a surfactant and a dispersant may be used. The surfactant includes anionic, nonionic, cationic and amphoteric surfactants, and any surfactant may be used, but an anionic or nonionic surfactant is preferably used. Examples of the anionic surfactant include a fatty acid salt, an alkylsulfuric ester salt, an alkylbenzenesulfonate, an alkylnaphthalenesulfonate, a dialkylsulfosuccinate, an alkyldiaryl ether disulfonate, an alkyl phosphate, a polyoxyethylene alkyl ether sulfate, a polyoxyethylene alkylaryl ether sulfate, a naphthalenesulfonic acid formalin condensate, a polyoxyethylene alkylphosphoric ester salt, a glycerol borate fatty acid ester and a polyoxyethylene glycerol fatty acid ester.

Examples of the nonionic surfactant include a polyoxyethylene alkyl ether, a polyoxyethylene alkylaryl ether, a polyoxyethylene oxypropylene block copolymer, a sorbitan fatty acid ester, a polyoxyethylene sorbitan fatty acid ester, a polyoxyethylene sorbitol fatty acid ester, a glycerin fatty acid ester, a polyoxyethylene fatty acid ester, a polyoxyethylene alkylamine, and fluorine-containing and silicon-containing surfactants.

The non-aqueous pigment dispersion is obtained by dispersing the pigment represented by formula (1) in a non-aqueous vehicle. Examples of the resin used for the non-aqueous vehicle include petroleum resin, casein, shellac, rosin-modified maleic acid resin, rosin-modified phenol resin, nitrocellulose, cellulose acetate butyrate, cyclized rubber, chlorinated rubber, oxidized rubber, hydrochlorinated rubber, phenol resin, alkyd resin, polyester resin, unsaturated polyester resin, amino resin, epoxy resin, vinyl resin, vinyl chloride, vinyl chloride-vinyl acetate copolymer, acrylic resin, methacrylic resin, polyurethane resin, silicon resin, fluororesin, drying oil, synthetic drying oil, styrene/maleic acid resin, styrene/acrylic resin, polyamide resin, polyimide resin, benzoguanamine resin, melamine resin, urea resin chlorinated polypropylene, butyral resin and vinylidene chloride resin. A photocurable resin may also be used as the non-aqueous vehicle.

Examples of the solvent used for the non-aqueous vehicle include an aromatic solvent such as toluene, xylene and methoxybenzene, an acetic acid ester-based solvent such as propylene, glycol monomethyl ether acetate and propylene glycol monoethyl ether acetate, a propionate-based solvent such as ethoxyethyl propionate, an alcohol-based solvent such as methanol and ethanol, an ether-based solvent such as butyl cellosolve, propylene glycol monomethyl ether, diethylene glycol ethyl ether and diethylene glycol dimethyl ether, a ketone-based solvent such as methyl ethyl ketone, methyl isobutyl ketone and cyclohexanone, an aliphatic hydrocarbon-based solvent such as hexane, a nitrogen compound-based solvent such as N,N-dimethylformamide, γ-butyrolactam, N-methyl-2-pyrrolidone, aniline and pyridine, a lactone-based solvent such as γ-butyrolactone, and a carbamic acid ester such as a 48:52 mixture of methyl carbamate and ethyl carbamate.

The pigment dispersion of the present invention is obtained by dispersing the above-described azo pigment and an aqueous or non-aqueous medium by means of a dispersing device. Examples of the dispersing device which can be used include a simple stirrer, an impeller stirring system, an in-line stirring system, a mill system (e.g., colloid mill, ball mill, sand mill, bead mill, attritor, roll mill, jet mill, paint shaker, agitator mill), an ultrasonic system, and a high-pressure emulsion dispersion system (e.g., high-pressure homogenizer; specifically, as the commercially available device, Gaulin homogenizer, Microfluidizer, DeBEE 2000).

In the present invention, the volume average particle diameter of the pigment is preferably from 10 to 250 nm. Incidentally, the volume average particle diameter of the pigment particle indicates the particle diameter of the pigment itself or when an additive such as dispersant is attached to the color material, the diameter of the particle to which the additive is attached. In the present invention, the device used for measuring the volume average particle diameter of the pigment was a Nanotrac UPA particle size distribution analyzer (UPA-EX150, manufactured by Nikkiso Co., Ltd.). The measurement was performed according to the predetermined measurement method after placing 3 ml of the pigment dispersion in the measurement cell. In this connection, as for the parameter input at the measurement, the ink viscosity was used for the viscosity, and the pigment density was used for the density of dispersed particles.

The volume average particle diameter is more preferably from 20 to 250 nm, still more preferably from 30 to 230 nm, and most preferably from 30 to 150 nm. When the volume average particle diameter of the particles in the pigment dispersion is 20 nm or more, the storage stability can be ensured, and when it is 250 nm or less, sufficient optical density is obtained.

The concentration of the pigment contained in the pigment dispersion of the present invention is preferably from 1 to 35 mass %, more preferably from 2 to 25 mass %, and most preferably from 5 to 15 mass %. When the concentration is 1 mass % or more, a sufficient image density is obtained in using the pigment dispersion alone as an ink, and when the concentration is 35 mass % or less, adequate dispersion stability is obtained.

The usage of the azo pigment of the present invention includes an image recording material for forming an image, particularly a color image, and specific examples thereof include an inkjet recording material described later in detail, a heat-sensitive recording material, a pressure-sensitive recording material, a recording material using an electrophotographic system, a transfer silver halide light-sensitive material, a printing ink, and a recording pen. Among these, an inkjet recording material, a heat-sensitive recording material and a recording material using an electrophotographic system are preferred, and an inkjet recording material is more preferred.

Also, the azo pigment is applicable to a color filter for recording and reproducing a color image, which is used in a solid imaging device such as CCD or in a display such as LCD or PDP, or to a dyeing solution for dyeing various fibers.

In using the azo pigment of the present invention, its physical properties suitable for usage, such as solvent resistance, dispersibility and thermal mobility, are adjusted by a substituent.

[Coloring Composition]

The coloring composition of the present invention means a coloring composition comprising at least one kind of the azo pigment of the present invention. The coloring composition of the present invention may contain a medium and when a solvent is used as the medium, the coloring composition is suitable particularly as an ink for inkjet recording. The coloring composition of the present invention can be produced by using a lipophilic medium or an aqueous medium as the medium and dispersing the azo pigment of the present invention in the medium. Use of an aqueous medium is preferred. The coloring composition of the present invention includes an ink composition after removing the medium. The coloring composition of the present invention may contain, if desired, other additives within the range not impairing the effects of the present invention. Examples of other additives include known additives (described in JP-A-2003-306623) such as drying inhibitor (wetting agent), discoloration inhibitor, emulsion stabilizer, penetration accelerator, ultraviolet absorber, antiseptic, fungicide, pH adjusting agent, surface tension adjusting agent, defoaming agent, viscosity adjusting agent, dispersant, dispersion stabilizer, rust inhibitor and chelating agent. These various additives are generally added, in the case of an aqueous ink, directly to the ink solution and, in the case of an oil-based ink, added to the dispersion after the preparation of an azo pigment dispersion but may be added to an oil phase or an aqueous phase at the preparation.

[Ink]

The ink of the present invention is described below.

The ink of the present invention contains the pigment dispersion of the present invention and is preferably prepared by mixing a water-soluble solvent, water or the like. However, if there is no problem in particular, the pigment dispersion of the present invention may be used as it is.

The ink for inkjet recording of the present invention contains the pigment dispersion of the present invention, and the ink of the present invention may also be used as the ink for inkjet recording.

The coloring composition containing the pigment of the present invention can be preferably used as the ink for inkjet recording.

The ink of the present invention uses the above-described pigment dispersion and is preferably prepared by mixing a water-soluble solvent, water or the like. However, if there is no problem in particular, the pigment dispersion of the present invention may be used as it is.

The ink of the present invention uses the above-described pigment dispersion and is preferably prepared by mixing a water-soluble solvent, water or the like. However, if there is no problem in particular, the pigment dispersion of the present invention may be used as it is.

[Ink for Inkjet Recording]

Next, the ink for inkjet recording is described below.

The ink for inkjet recording (hereinafter sometimes referred to as "ink") uses the above-described pigment dispersion and is preferably prepared by mixing a water-soluble solvent, water or the like. However, if there is no problem in particular, the pigment dispersion of the present invention may be used as it is.

The ratio of the pigment dispersion contained in the ink is, in view of hue, color density, saturation, transparency and the like of the image formed on a recording medium, preferably from 1 to 100 mass %, more preferably from 3 to 20 mass %, and most preferably from 3 to 10 mass %.

The ink preferably contains the azo pigment of the present invention in an amount of 0.1 to 20 parts by mass, more preferably from 0.2 to 10 parts by mass, still more preferably from 1 to 10 parts by mass, per 100 parts by mass of the ink. In the ink of the present invention, other pigments may be used in combination with the pigment of the present invention. In the case of using two or more kinds of pigments, the total of pigment contents is preferably in the range above.

The ink can be used not only for the formation of a monochromatic image but also for the formation of a full color image. For forming a full color image, a magenta tone ink, a cyan tone ink and a yellow tone ink can be used. Also, for adjusting the color tone, a black tone ink may be further used.

In the ink of the present invention, a different pigment can be used at the same time in addition to the azo pigment of the present invention. Examples of the applicable yellow pigment include C.I.P.Y.-74, C.I.P.Y.-128, C.I.P.Y.-155 and C.I.P.Y.-213; examples of the applicable magenta pigment include C.I.P.V.-19 and C.I.P.R.-122; and examples of the applicable cyan pigment include C.I.P.B.-15:3 and C.I.P.B.-15:4. Other than these pigments, an arbitrary pigment can be used. Examples of the applicable black color material include disazo, trisazo and tetrazo pigments and a carbon black dispersion.

Examples of the water-soluble solvent used in the ink include polyhydric alcohols, polyhydric alcohol derivatives, a nitrogen-containing solvent, alcohols, and a sulfur-containing solvent.

Specific examples of the polyhydric alcohols include ethylene glycol, diethylene glycol, propylene glycol, butylene glycol, triethylene glycol, 1,5-pentanediol, 1,2,6-hexanetriol and glycerin.

Specific examples of the polyhydric alcohol derivatives include ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, propylene glycol monobutyl ether, dipropylene glycol monobutyl ether, and an ethylene oxide adduct of diglycerin.

Specific examples of the nitrogen-containing solvent include pyrrolidone, N-methyl-2-pyrrolidone, cyclohexylpyrrolidone and triethanolamine; specific examples of the alcohols include alcohols such as ethanol, isopropyl alcohol, butyl alcohol and benzyl alcohol; and specific examples of the sulfur-containing solvent include thiodiethanol, thiodiglycerol, sulfolane and dimethylsulfoxide. In addition, propylene carbonate, ethylene carbonate and the like may be used.

As for the water-soluble solvent used in the present invention, one kind of a solvent may be used alone, or two or more kinds of solvents may be mixed and used. The content of the water-soluble solvent used is from 1 to 60 mass %, preferably from 5 to 40 mass %, based on the entire ink. If the amount of the water-soluble solvent in the ink is less than 1 mass %, sufficient optical density is sometimes not obtained, whereas if it exceeds 60 mass %, the viscosity of the liquid is increased and jetting characteristics of the ink liquid becomes unstable in some cases.

Preferred physical properties of the ink of the present invention are as follows. The surface tension of the ink is preferably from 20 to 60 mN/m, more preferably from 20 to 45 mN/m, still more preferably from 25 to 35 mN/m. If the surface tension is less than 20 mN/m, the liquid overflows on the nozzle surface of the recording head and the printing may not be normally performed, whereas if it exceeds 60 mN/m, penetration into the recording medium after printing proceeds slowly and the drying time may become longer. The surface tension above was measured in an environment of 23° C. and 55% RH by using a Wilhelmy surface tensiometer similarly.

The viscosity of the ink is preferably from 1.2 to 8.0 mPa·s, more preferably from 1.5 to 6.0 mPa·s, still more preferably from 1.8 to 4.5 mPa·s. If the viscosity exceeds 8.0 mPa·s, the ejection performance sometimes deteriorates, whereas if it is less than 1.2 mPa·s, the long-term jetting performance becomes worse in some cases.

Incidentally, the above-described viscosity (including those described later) was measured using rotational viscometer Rheomat 115 (manufactured by Contraves) at 23° C. and a shear velocity of 1,400 $s^{-1}$.

In the ink, water is added within the range giving the above-described preferred surface tension and viscosity, in addition to the components above. The amount of water added is not particularly limited but is preferably from 10 to 99 mass %, more preferably from 30 to 80 mass %, based on the entire ink.

For the purpose of characteristic control such as improvement of ejection performance, polyethyleneimine, polyamines, polyvinylpyrrolidone, polyethylene glycol, cellulose derivatives such as ethyl cellulose and carboxymethyl cellulose, polysaccharides and derivates thereof, other water-soluble polymers, polymer emulsions such as acrylic polymer emulsion, polyurethane-based emulsion and hydrophilic latex, hydrophilic polymer gel, cyclodextrin, macrocyclic amines, dendrimer, crown ethers, urea and derivatives thereof, acetamide, a silicone-containing surfactant, a fluorine-containing surfactant and the like can be further used, if desired.

Also, for adjusting the electrical conductivity and pH, alkali metal compounds such as potassium hydroxide, sodium hydroxide and lithium hydroxide, nitrogen-containing compounds such as ammonium hydroxide, triethanolamine, diethanolamine, ethanolamine and 2-amino-2-methyl-1-propanol, alkaline earth metal compounds such as calcium hydroxide, acids such as sulfuric acid, hydrochloric acid and nitric acid, salts of strong acid and weal alkali, such as ammonium sulfate, and the like can be used.

In addition, a pH buffering agent, an antioxidant, a fungicide, a viscosity adjusting agent, an electrical conducting agent, an ultraviolet absorber and the like may be added, if desired.

[Inkjet Recording Method, Inkjet Recording Apparatus and Ink Tank for Inkjet Recording]

The inkjet recording method is a method for forming an image on a recording medium surface by using the ink for inkjet recording and ejecting the ink on a recording medium surface from a recording head according to recording signals.

The inkjet recording apparatus is an apparatus for forming an image by using an ink for inkjet recording and includes a recording head for ejecting the ink (if desired, a treated solution) on a recording medium surface, where the ink is ejected from the recording head on a recording medium surface and an image is thereby formed. Incidentally, the inkjet recording apparatus may include an ink tank for inkjet recording (sometimes referred to as an "ink tank"), which can supply the ink to the recording head and is detachable from the body of the inkjet recording apparatus. In this case, the ink is housed in the ink tank for inkjet recording.

As for the inkjet recording apparatus, a normal inkjet recording apparatus equipped with a printing system capable of using an ink for inkjet recording can be utilized, and furthermore, a heater or the like for controlling the drying of the ink or an intermediate transfer mechanism, that is, a mechanism of ejecting (printing) the ink or a treated solution on an intermediate and then transferring it on a recording medium such as paper, may be mounted, if desired.

As regards the ink tank for inkjet recording, a conventionally known ink tank can be utilized as long as it is detachable from the inkjet recording apparatus with a recording head and has a configuration capable of supplying the ink to the recording head in the state of being loaded in the inkjet recording apparatus.

In view of the effect of improving bleed and intercolor bleed, the inkjet recording method (apparatus) preferably employs a thermal inkjet recording system or a piezoelectric inkjet recording system. In the case of the thermal inkjet recording system, the ink is heated at the ejection to allow for low viscosity, but since the temperature of the ink lowers on a recording medium, the viscosity is abruptly increased, and this is effective in improving bleed and intercolor bleed. On the other hand, in the case of the piezoelectric inkjet system, a liquid with high viscosity can be ejected, and the high-viscosity liquid can be kept from spreading in the paper surface direction on a recording medium, which is effective in improving bleed and intercolor bleed.

In the inkjet recording method (apparatus), the ink is preferably replenished (supplied) to the recording head from an ink tank (if desired, including a treated solution tank) filled with an ink solution. This ink tank is preferably a cartridge system detachable from the body of the apparatus, and by replacing this ink tank cartridge, replenishment of the ink is easily performed.

[Color Toner]

The azo pigment is not particularly limited in its content per 100 parts by mass of a color toner but is preferably contained in an amount of 0.1 parts by mass or more, more preferably from 1 to 20 parts by mass, and most preferably from 2 to 10 parts by mass. As regards the binder resin for color toner, in which the azo pigment is introduced, all of binders employed in general can be used. Examples thereof include a styrene-based resin, an acrylic resin, a styrene/acrylic resin and a polyester resin.

For enhancing the flowability, controlling the electrostatic charge or other purposes, an inorganic fine powder or an organic fine particle may be externally added to the toner. A silica or titania fine particle whose surface is treated with an alkyl group-containing coupling agent or the like is preferably used. Such a fine powder or particle preferably has a number average primary particle diameter of 10 to 500 nm and is preferably added in an amount of 0.1 to 20 mass % based on the toner.

As for the releasing agent, conventionally employed releasing agents all can be used. Specific examples thereof include olefins such as low molecular weight propylene, low molecular weight polyethylene and ethylene-propylene copolymer, microcrystalline wax, carnauba wax, sazole wax and paraffin wax. The releasing agent is preferably added in an amount of 1 to 5 mass % to the toner.

The charge controlling agent may be added, if desired, but in view of color formation, a colorless charge controlling agent is preferred. Examples thereof include those having a quaternary ammonium salt structure and those having a calix arene structure.

The carrier may be either a non-coated carrier composed of only a magnetic material particle such as iron and ferrite, or a resin-coated carrier obtained by coating the surface of a magnetic material particle with resin or the like. The average particle diameter of this carrier is preferably from 30 to 150 µm in terms of the volume average particle diameter.

The image forming method to which the toner is applied is not particularly limited, but examples thereof include a method of repeatedly forming a color image on a photoreceptor and then transferring the color images, thereby forming an image, and a method of sequentially transferring the image formed on a photoreceptor to an intermediate transfer material or the like to form a color image on the intermediate transfer material or the like and then transferring the image on an image-forming member such as paper.

[Heat-Sensitive Recording (Transfer) Material]

The heat-sensitive recording material is composed of an ink sheet comprising a support having coated thereon the azo pigment of the present invention together with a binder, and an image-receiving sheet for immobilizing the pigment transferred in response to the thermal energy added from a thermal head according to image-recording signals. The ink sheet can be formed by dispersing the azo pigment of the present invention in a solvent together with a binder in the form of fine particles to prepare an ink solution, coating the ink on a support, and appropriately drying it. The amount of the ink coated on the support is not particularly limited but is preferably from 30 to 1,000 mg/m². As for preferred binder resins, ink solvents, supports and further, image-receiving sheets, those described in JP-A-7-137466 can be preferably used.

In applying the heat-sensitive recording material as a heat-sensitive recording material capable of recording a full color image, the recording material is preferably formed by sequentially coating, on a support, a cyan ink sheet containing a heat-diffusible cyan colorant capable of forming a cyan image, a magenta ink sheet containing a heat-diffusible magenta colorant capable of forming a magenta image, and a yellow ink sheet containing a heat-diffusible yellow colorant capable of forming a yellow image. Also, an ink sheet containing a black image-forming substance may be additionally formed, if desired.

[Color Filter]

The method for forming a color filter includes a method of first forming a pattern by a photoresist and then dyeing it, and as described in JP-A-4-163552, JP-A-4-128703 and JP-A-4-175753, a method of forming a pattern by a photoresist having added thereto a colorant. As for the method used when introducing the colorant of the present invention into a color filter, any of those methods may be employed, but the preferred method includes a color filter forming method described in JP-A-4-175753 or JP-A-6-35182, where a positive resist composition containing a thermosetting resin, a quinonediazide compound, a crosslinking agent, a colorant and a solvent is coated on a substrate, the coating is exposed through a mask, the exposed area is developed to form a positive resist pattern, the positive resist pattern is entirely exposed, and the positive resist pattern after exposure is cured. Furthermore, an RGB primary color-based or YMC complementary color-based color filter can be obtained by forming a black matrix according to a conventional manner. Also in the case of a color filter, the amount used of the azo pigment of the present invention is not limited but is preferably from 0.1 to 50 mass %.

As for the thermosetting resin, quinonediazide compound, crosslinking agent and solvent used here and the amounts thereof, those described in the above-described patent documents can be preferably used.

The present invention is described in greater detail below by referring to Examples, but the present invention is not limited to these Examples. In Examples, "parts" indicates "parts by mass".

EXAMPLES

The X-ray diffraction measurement of the pigment composition of the present invention was performed in accordance with Japanese Industrial Standards JIS K0131 (General Rule of X-ray Diffraction Analysis) in a powder X-ray diffraction measuring apparatus, RINT2500 (manufactured by Rigaku Corporation), by using CuKα, line under the following conditions.
Measuring instrument used: Automatic X-ray diffraction apparatus, RINT2500, manufactured by Rigaku Corporation
X-ray tube: Cu
Tube voltage: 55 KV
Tube current: 280 mA
Scanning method: 2θ/θ Scan
Scanning speed: 6 deg./min
Sampling interval: 0.100 deg.
Starting angle (2θ): 5 deg.
Stopping angle (2θ): 55 deg.
Divergence slit: 2 deg.
Scattering slit: 2 deg.
Receiving slit: 0.6 mm
A vertical goniometer was used.

Synthesis Example 1

Synthesis of α-Type Crystal Morphology Azo Pigment

A synthesis scheme of an α-type crystal morphology azo pigment is shown below.

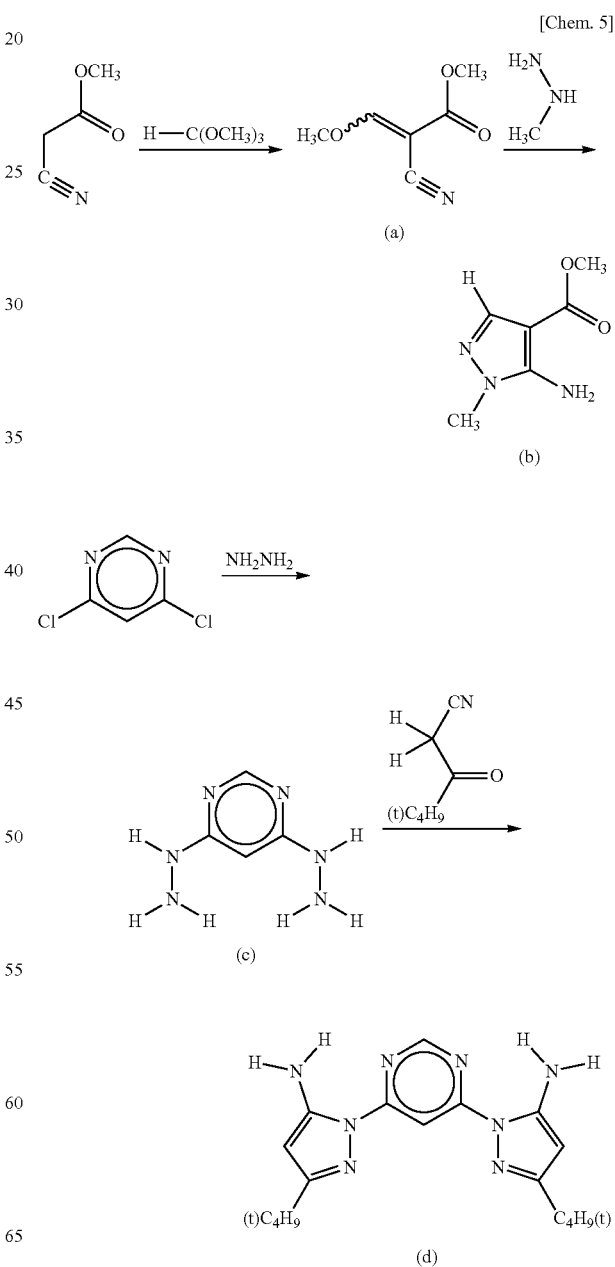

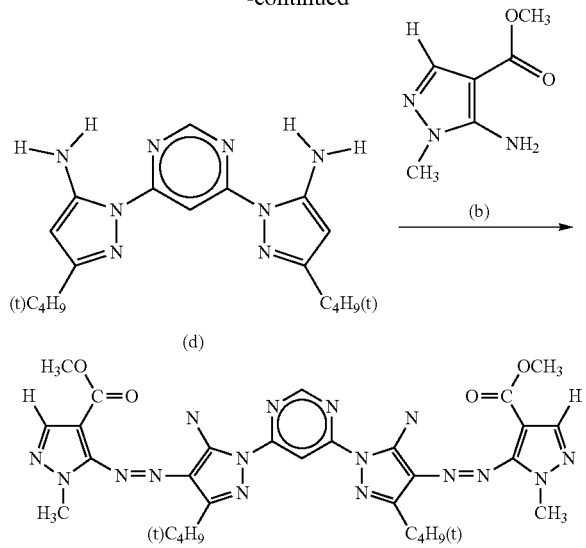

(1) Synthesis of Intermediate (a)

Trimethyl o-formate (42.4 g (0.4 mol)), 20.4 g (0.2 mol) of acetic anhydride and 0.5 g of p-toluenesulfonic acid were added to 29.7 g (0.3 mol) of methyl cyanoacetate, and the mixture was heated at 110° C. (external temperature) and stirred for 20 hours while distilling off low boiling-point components produced from the reaction system. The resulting reaction solution was concentrated under reduced pressure and then subjected to silica gel column purification to obtain 14.1 g of Intermediate (a) (yellow powder, yield: 30%). The NMR measurement results of Intermediate (a) obtained are as follows. $^1$H-NMR (300 MHz, CDCl$_3$) 7.96 (s, 1H), 4.15 (s, 3H), 3.81 (s, 3H).

(2) Synthesis of Intermediate (b)

Isopropanol (150 mL) was added to 7.4 mL (141 mmol) of methylhydrazine, and the mixture was cooled to 15° C. (internal temperature). To this mixed solution, 7.0 g (49.6 mmol) of Intermediate (a) was gradually added, and the resulting solution was heated at 50° C. and stirred for 1 hour and 40 minutes. The obtained reaction solution was concentrated under reduced pressure and then subjected to silica gel column purification to obtain 10.5 g of Intermediate (b) (white powder, yield: 50%). The NMR measurement results of Intermediate (b) obtained are as follows. $^1$H-NMR (300 MHz, CDCl$_3$) 7.60 (s, 1H), 4.95 (brs, 2H), 3.80 (s, 3H), 3.60 (s, 3H).

(3) Synthesis of Intermediate (c)

Methanol (298 mL) was added to 387 mL (7.98 mol) of hydrazine monohydrate, and the mixture was cooled to 10° C. (internal temperature). To this mixed solution, 149 g (1.00 mol) of 4.6-dichloropyrimidine was gradually added (internal temperature: 20° C. or less), and the ice bath was removed. The temperature was raised to room temperature, and the mixture was stirred at the same temperature for 30 minutes, then further heated to raise the temperature to an internal temperature of 60° C., and stirred at the same temperature for 5 hours. After the completion of reaction, 750 mL of water was added, and the resulting solution was cooled by ice cooling until the internal temperature became 8° C. The precipitated crystal was collected by filtration, spray-washed with water, further spray-washed with isopropanol and dried at room temperature for 36 hours to obtain 119 g of Intermediate (c) (white powder, yield: 84.5%). The NMR measurement results of Intermediate (c) obtained are as follows. $^1$H-NMR (300 MHz, d-DMSO) 7.80 (s, 1H), 7.52 (s, 2H), 5.98 (s, 1H), 4.13 (s, 4H).

(4) Synthesis of Intermediate (d)

Water (128 mL) was added to 50 g (357 mmol) of Intermediate (c), and the mixture was stirred at room temperature. To this suspension, 98.2 g (785 mmol) of pivaloylacetonitrile was added, and aqueous 12 M hydrochloric acid was added dropwise at the same temperature to adjust the pH to 3. Thereafter, the resulting mixture was heated until the interior temperature became 50° C., and stirred at the same temperature for 6 hours. After the completion of reaction, the reaction solution was neutralized by adding an aqueous 8N potassium hydroxide solution to a pH of 6.4 and then cooled by ice cooling until the internal temperature became 10° C. The precipitated crystal was collected by filtration and spray-washed with water, and the obtained crystal was dried at 60° C. under reduced pressure. To the obtained crude product, 30 mL of toluene was added, and the mixture was dissolved under heating at 60° C. The resulting solution was left standing still at room temperature for 12 hours, and the precipitated crystal was collected by filtration, spray-washed with cooled toluene and dried at 60° C. under reduced pressure to obtain 87.7 g of Intermediate (d) (white powder, yield: 69.3%). The NMR measurement results of Intermediate (d) obtained are as follows. $^1$H NMR (300 MHz, d-DMSO) 8.74 (s, 1H), 7.99 (s, 1H), 6.87 (s, 4H), 5.35 (s, 2H), 1.24 (s, 18H).

(5) Synthesis of α-Type Crystal Morphology Azo Pigment

[Chem. 6]

Formula (2):

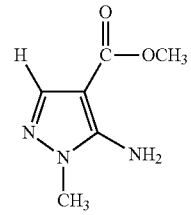

Formula (3):

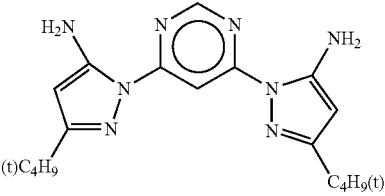

Formula (I):

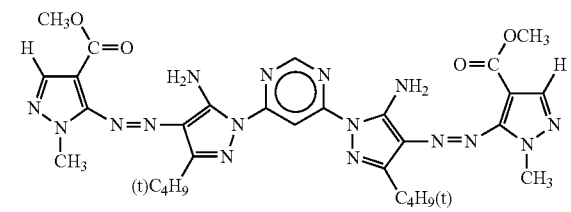

Compound (2) (9.2 g) was dissolved in a mixed solution of 55 mL of acetic acid and 37 mL of propionic acid at room temperature, and the resulting solution was ice-cooled to lower the internal temperature to −3° C. A 40 mass % sulfuric acid solution of nitrosylsulfuric acid was added dropwise at an internal temperature of −3° C. to 4° C. over 10 minutes and after stirring at an internal temperature of 4° C. for 1 hour, 0.2 g of urea was added. Thereafter, the internal temperature was lowered to −3° C., and the mixture was further stirred for 10 minutes to obtain a diazonium salt solution. Separately, 10 g of Compound (3) was completely dissolved in 150 mL of acetone. This solution was cooled to an internal temperature of 17° C. and then added to the diazonium salt solution obtained above, at an internal temperature of −3° C. to 3° C. over 25 minutes. After the completion of addition, the mixture was stirred at 3° C. for 30 minutes, and the ice bath was removed. The temperature was raised to room temperature over 30 minutes, and the resulting solution was stirred at room temperature for 30 minutes. The obtained crystal was collected by filtration, spray-washed with 150 mL of acetone and further spray-washed with 100 mL of water. The obtained crystal was without drying suspended in 400 mL of water, and an aqueous 8 N potassium hydroxide solution was added to adjust the pH to 5.7. The system was stirred at room temperature for 20 minutes, and the obtained crystal was separated by filtration, thoroughly spray-washed with water and spray-washed with 80 mL of acetone. The obtained crystal was dried at room temperature for 12 hours.

Crystal 1 obtained was suspended in 580 mL of acetone, and the suspension was stirred under reflux for 30 minutes and then cooled to room temperature over 10 minutes. The obtained crystal was separated by filtration and dried at 60° C. for 5 hours to obtain 17.1 g of an azo pigment composition containing an azo pigment represented by formula (1) having the crystal form of the present invention. Yield: 88.5%. The particle size of the obtained azo pigment was measured with an eye by using a transmission microscope (electron microscope JEM-1010, manufactured by JEOL Ltd.), as a result, the length in the long axis direction of the primary particle was about 15 μm.

The obtained crystal was an α-type crystal morphology azo pigment shown in FIG. 1 or a tautomer thereof, having characteristic X-ray diffraction peaks at Bragg angles (2θ±0.2°) of 7.6°, 25.6° and 27.7° in the CuKα characteristic X-ray diffraction but not having a peak at 7.0° and 6.4° (α-Type Crystal Morphology Azo Pigment Composition 1).

Synthesis Example 2

Synthesis of β-Type Crystal Morphology Azo Pigment

Compound (2) (9.2 g) was dissolved in a mixed solution of 55 mL of acetic acid and 37 mL of propionic acid at room temperature, and the resulting solution was ice-cooled to lower the internal temperature to −3° C. A 40 mass % sulfuric acid solution of nitrosylsulfuric acid was added dropwise at an internal temperature of −3° C. to 4° C. over 10 minutes and after stirring at an internal temperature of 4° C. for 1 hour, 0.2 g of urea was added. Thereafter, the internal temperature was lowered to −3° C., and the mixture was further stirred for 10 minutes to obtain a diazonium salt solution. Separately, 10 g of Compound (3) was completely dissolved in 150 mL of acetone. This solution was cooled to an internal temperature of 17° C. and then added to the diazonium salt solution obtained above, at an internal temperature of −3° C. to 3° C. over 25 minutes. After the completion of addition, the mixture was stirred at 3° C. for 30 minutes, and the ice bath was removed. The temperature was raised to room temperature over 30 minutes, and the resulting solution was stirred at room temperature for 30 minutes. The obtained crystal was collected by filtration, spray-washed with 150 mL of acetone and further spray-washed with 100 mL of water. The obtained crystal was without drying suspended in 400 mL of water, and an aqueous 8 N potassium hydroxide solution was added to adjust the pH to 5.7. The system was stirred at room temperature for 25 minutes, and the obtained crystal was separated by filtration, thoroughly spray-washed with water and spray-washed with 80 mL of acetone. The obtained crystal was dried at room temperature for 12 hours.

Crystal 2 obtained was suspended in a mixed solvent of 580 mL of acetone and 1,160 mL of water, and the suspension was stirred under reflux for 30 minutes and then cooled to room temperature over 10 minutes. The obtained crystal was separated by filtration and dried at 60° C. for 5 hours to obtain 17.6 g of an azo pigment represented by formula (1) having the crystal form of the present invention. Yield: 91.0%. The particle size of the obtained azo pigment was measured with an eye by using a transmission microscope (electron microscope JEM-1010, manufactured by JEOL Ltd.), as a result, the length in the long axis direction of the primary particle was about 150 nm.

Figure 2:
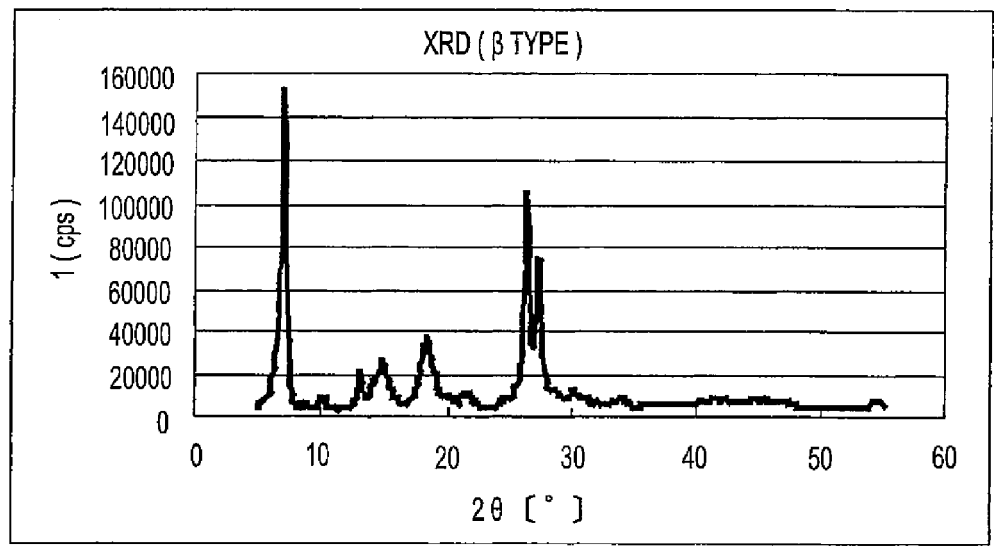
FIG. 2 A view showing the X-ray diffraction of Azo Pigment Composition 2 of β-type crystal morphology synthesized in accordance with Synthesis Example 2.
Figure 3:
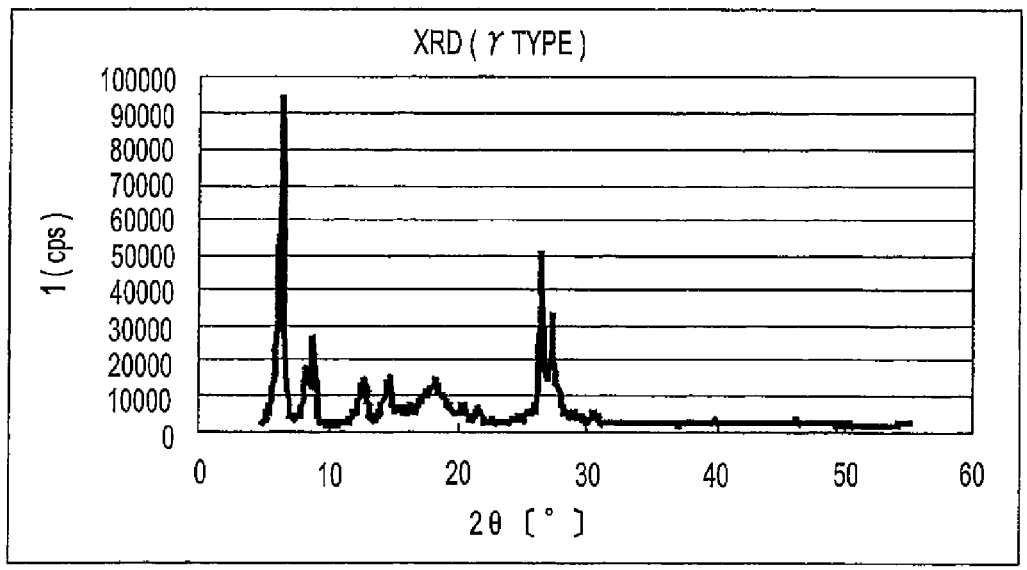
FIG. 3 A view showing the X-ray diffraction of Azo Pigment Composition 3 of γ-type crystal morphology synthesized in accordance with Synthesis Example 3.

The obtained crystal was a β-type crystal morphology azo pigment shown in FIG. 2 or a tautomer thereof, having characteristic X-ray diffraction peaks at Bragg angles (2θ±0.2°) of 7.0°, 26.4° and 27.3° in the CuKα characteristic X-ray diffraction but not having a peak at 6.4° and 7.6° (β-Type Crystal Morphology Azo Pigment Composition 2).

Synthesis Example 3

Synthesis of γ-Type Crystal Morphology Azo Pigment

Compound (2) (9.2 g) was dissolved in a mixed solution of 55 mL of acetic acid and 37 mL of propionic acid at room temperature, and the resulting solution was ice-cooled to lower the internal temperature to −3° C. A 40 mass % sulfuric acid solution of nitrosylsulfuric acid was added dropwise at an internal temperature of −3° C. to 4° C. over 10 minutes and after stirring at an internal temperature of 4° C. for 1 hour, 0.2 g of urea was added. Thereafter, the internal temperature was lowered to −3° C., and the mixture was further stirred for 10 minutes to obtain a diazonium salt solution. Separately, 11.1 g of Compound (3) was completely dissolved in 160 mL of acetone. This solution was cooled to an internal temperature of 17° C. and then added to the diazonium salt solution obtained above, at an internal temperature of −3° C. to 3° C. over 25 minutes. After the completion of addition, the mixture was stirred at 3° C. for 30 minutes, and the ice bath was removed. The temperature was raised to room temperature over 30 minutes, and the resulting solution was stirred at room temperature for 30 minutes. The obtained crystal was collected by filtration, spray-washed with 150 mL of acetone and further spray-washed with 100 mL of water. The obtained crystal was without drying suspended in 400 mL of water, and an aqueous 8 N potassium hydroxide solution was added to adjust the pH to 6.7. The system was stirred at room temperature for 25 minutes, and the obtained crystal was separated by filtration, thoroughly spray-washed with water and spray-washed with 80 mL of acetone. The obtained crystal was dried at room temperature for 12 hours.

Crystal 3 obtained was suspended in 500 mL of acetone, and the suspension was stirred under reflux for 30 minutes and then cooled to room temperature over 1 hour. The obtained crystal was separated by filtration and dried at 60° C. for 5 hours to obtain 17.4 g of an azo pigment represented by formula (1) having the crystal form of the present invention. Yield: 81.0%. The particle size of the obtained azo pigment was measured with an eye by using a transmission microscope (electron microscope JEM-1010, manufactured by JEOL Ltd.), as a result, the length in the long axis direction of the primary particle was about 300 nm.

The obtained crystal was a γ-type crystal morphology azo pigment or a tautomer thereof, having characteristic X-ray diffraction peaks at Bragg angles (2θ±0.2°) of 6.4°, 26.4° and 27.2° in the CuKα characteristic X-ray diffraction but not having a peak at 7.0° and 7.6° (γ-Type Crystal Morphology Azo Pigment Composition 3).

Example 1

Synthesis of Azo Pigment Composition Containing α,β-Mixed Crystal Morphology Azo Pigment Crystal 1 obtained in Synthesis Example 1 was suspended in 580 mL of methanol, and the suspension was stirred under reflux for 30 minutes and then cooled to room temperature over 30 minutes. The obtained crystal was separated by filtration and dried at room temperature for 5 hours to obtain 17.1 g of an azo pigment composition containing an azo pigment represented by formula (1) having the crystal form of the present invention. Yield: 88.5%. The particle size of the obtained azo pigment was measured with an eye by using a transmission microscope (electron microscope JEM-1010, manufactured by JEOL Ltd.), as a result, the length in the long axis direction of the primary particle was about 10 μm.

Figure 4:
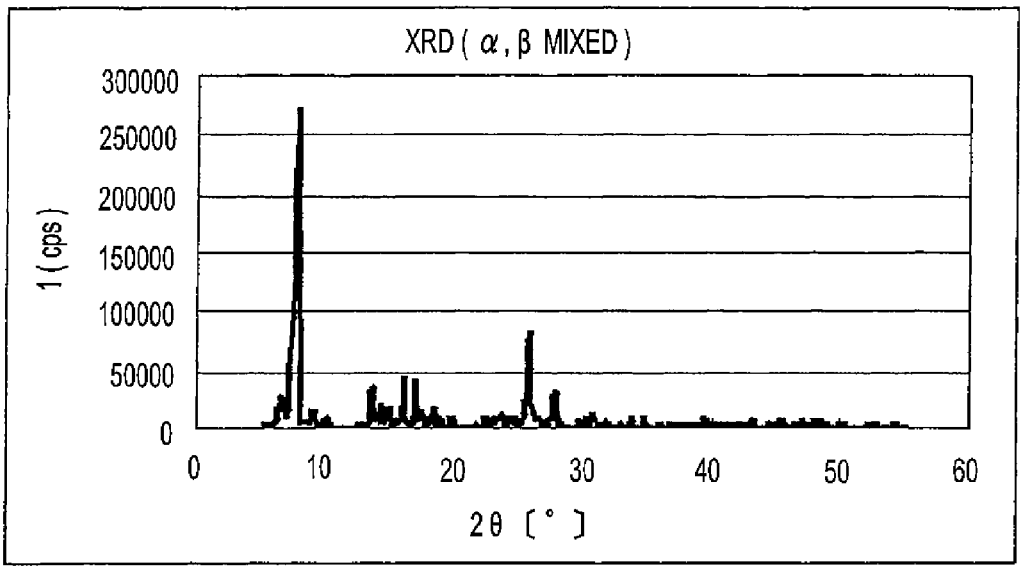
FIG. 4 A view showing the X-ray diffraction of Azo Pigment Composition 4 synthesized in accordance with Example 1.

The azo pigment composition was Azo Pigment Composition 4 shown in FIG. 4 containing, as the main component, an α-type crystal morphology azo pigment or a tautomer thereof, having characteristic X-ray diffraction peaks at Bragg angles (2θ±0.2°) of 7.6°, 25.6° and 27.7° in the CuKα characteristic X-ray diffraction, and further containing a β-type crystal morphology azo pigment or a tautomer thereof, having characteristic X-ray diffraction peaks at Bragg angles (2θ±0.2°) of 7.0°, 26.4° and 27.3° in the CuKα characteristic X-ray diffraction.

Example 11

Production of Pigment Dispersion 1

2.5 Parts of α-type crystal morphology Azo Pigment Composition (1) synthesized in Synthesis Example 1, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 2 hours. After the completion of dispersion, zirconia beads were separated to obtain yellow Pigment Dispersion 1 (average particle diameter: Mv=about 67 nm, as measured using Nanotrac 150 (UPA-EX150) manufactured by Nikkiso Co., Ltd.).

Example 12

Production of Pigment Dispersion 2

2.25 Parts of α-type crystal morphology Azo Pigment Composition (1) synthesized in Synthesis Example 1, 0.25 parts of β-type crystal morphology Azo Pigment Composition (2) synthesized in Synthesis Example 2, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 3 hours. After the completion of dispersion, zirconia beads were separated to obtain yellow Pigment Dispersion 2 (average particle diameter: Mv=about 64 nm, as measured using Nanotrac 150 (UPA-EX150) manufactured by Nikkiso Co., Ltd.).

Example 13

Production of Pigment Dispersion 3

2.0 Parts of α-type crystal morphology Azo Pigment Composition (1) synthesized in Synthesis Example 1, 0.5 parts of β-type crystal morphology Azo Pigment Composition (2) synthesized in Synthesis Example 2, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 3 hours. After the completion of dispersion, zirconia beads were separated to obtain yellow Pigment Dispersion 3 (average particle diameter: Mv=about 68 nm, as measured using Nanotrac 150 (UPA-EX150) manufactured by Nikkiso Co., Ltd.).

Example 14

Production of Pigment Dispersion 4

1.5 Parts of α-type crystal morphology Azo Pigment Composition (1) synthesized in Synthesis Example 1, 1.0 parts of β-type crystal morphology Azo Pigment Composition (2) synthesized in Synthesis Example 2, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 3 hours. After the completion of dispersion, zirconia beads were separated to obtain yellow Pigment Dispersion 4 (average particle diameter: Mv=about 67 nm, as measured using Nanotrac 150 (UPA-EX150) manufactured by Nikkiso Co., Ltd.).

Example 15

Production of Pigment Dispersion 5

1.25 Parts of α-type crystal morphology Azo Pigment Composition (1) synthesized in Synthesis Example 1, 1.25 parts of β-type crystal morphology Azo Pigment Composition (2) synthesized in Synthesis Example 2, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 3 hours. After the completion of dispersion, zirconia beads were separated to obtain yellow Pigment Dispersion 5 (average particle diameter: Mv=about 70 nm, as measured using Nanotrac 150 (UPA-EX150) manufactured by Nikkiso Co., Ltd.).

Example 16

Production of Pigment Dispersion 6

2.25 Parts of α-type crystal morphology Azo Pigment Composition (1) synthesized in Synthesis Example 1, 0.25 parts of γ-type crystal morphology Azo Pigment Composition (3) synthesized in Synthesis Example 3, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 3 hours. After the completion of dispersion, zirconia beads were separated to obtain yellow Pigment Dispersion 6 (average particle diameter: Mv=about 65 nm, as measured using Nanotrac 150 (UPA-EX150) manufactured by Nikkiso Co., Ltd.).

Example 17

Production of Pigment Dispersion 7

2.0 Parts of α-type crystal morphology Azo Pigment Composition (1) synthesized in Synthesis Example 1, 0.5 parts of γ-type crystal morphology Azo Pigment Composition (3) synthesized in Synthesis Example 3, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 3 hours. After the completion of dispersion, zirconia beads were separated to obtain yellow Pigment Dispersion 7 (average particle diameter: Mv=about 66 nm, as measured using Nanotrac 150 (UPA-EX150) manufactured by Nikkiso Co., Ltd.).

Example 18

Production of Pigment Dispersion 8

1.5 Parts of α-type crystal morphology Azo Pigment Composition (1) synthesized in Synthesis Example 1, 1.0 parts of γ-type crystal morphology Azo Pigment Composition (3) synthesized in Synthesis Example 3, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 3 hours. After the completion of dispersion, zirconia beads were separated to obtain yellow Pigment Dispersion 8 (average particle diameter: Mv=about 68 nm, as measured using Nanotrac 150 (UPA-EX150) manufactured by Nikkiso Co., Ltd.).

Example 19

Production of Pigment Dispersion 9

1.25 Parts of α-type crystal morphology Azo Pigment Composition (1) synthesized in Synthesis Example 1, 1.25 parts of γ-type crystal morphology Azo Pigment Composition (3) synthesized in Synthesis Example 3, 0.5 parts of sodium oleate, 5 parts of glycerin and 42 parts of water were mixed, and the mixture was dispersed together with 100 parts of zirconium beads having a diameter of 0.1 nun by using a planetary ball mill at 300 rpm for 3 hours. After the completion of dispersion, zirconia beads were separated to obtain yellow Pigment Dispersion 9 (average particle diameter: Mv=about 72 nm, as measured using Nanotrac 150 (UPA-EX150) manufactured by Nikkiso Co., Ltd.).

Example 20

Production of Pigment Dispersion 10

2.5 Parts of Azo Pigment Composition (4) synthesized in Example 1, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 2 hours. After the completion of dispersion, zirconia beads were separated to obtain yellow Pigment Dispersion 10 (average particle diameter: Mv=about 60 nm, as measured using Nanotrac 150 (UPA-EX150) manufactured by Nikkiso Co., Ltd.).

Comparative Example 1

Production of Comparative Pigment Dispersion 1

Yellow Comparative Pigment Dispersion 1 was obtained in the same manner as in Synthesis Example 1 except for using C.I. Pigment Yellow 74 (Iralite YELLOW GO, produced by Ciba Specialty) in place of α-type crystal morphology Azo Pigment Composition (1) used in Synthesis Example 1.

Comparative Example 2

Production of Comparative Pigment Dispersion 2

Yellow Comparative Pigment Dispersion 2 was obtained in the same manner as in Synthesis Example 1 except for using C.I. Pigment Yellow 155 (INKJET YELLOW 4G VP2532, produced by Clariant) in place of α-type crystal morphology Azo Pigment Composition (1) used in Synthesis Example 1.

Comparative Example 3

Production of Comparative Dispersion 3

The same operation as in Synthesis Example 1 was performed except for using Compound (DYE-1) shown below in place of α-type crystal morphology Azo Pigment Composition (1) used in Synthesis Example 1, as a result, the compound was dissolved and could not be dispersed.

[Chem. 7]

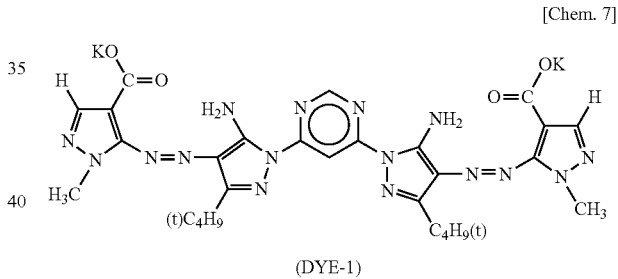

(DYE-1)

<Dispersibility>

Pigment Dispersions 1 to 10 of the present invention, Comparative Pigment Dispersions 1 and 2, and Comparative Dispersion 3 were evaluated by mixing 2.5 parts of pigment, 0.5 parts of sodium oleate, 5 parts of glycerin and 42 parts of water and dispersing the mixture together with 100 parts of zirconium beads having a diameter of 0.1 mm in a planetary ball mill at 300 rpm for 2 hours, and rated X when coarse particles of 100 nm or more were observed, rated X X when failed in dispersing, or rated ○ when coarse particles were scarcely observed. The results are shown in Table 1.

<Dispersion Stability>

The pigment dispersions obtained in Examples 11 to 20 and Comparative Examples 1 and 2 were left standing still at room temperature for 4 weeks and rated X when a precipitate was observed with an eye, or rated ○ when a precipitate was not observed. The results are shown in Table 1.

<Evaluation of Hue>

The hue was evaluated by observing with an eye the chromaticity of the coated material obtained above and rated ⊚ (good) when little tinting with green and high clearness were recognized, rated ○ when either one was lacking, or rated X (bad) when both were lacking. The results are shown in Table 1.

<Evaluation of Tinctorial Strength>

The pigment dispersions obtained in Examples 11 to 20 and Comparative Examples 1 and 2 each was coated on photomat paper produced by Seiko Epson Corporation by using a No. 3 bar coater. The coated material obtained was measured using a reflection densitometer (X-Rite 938, manufactured by X-Rite), and the "tinctorial strength (OD: Optical Density)" was evaluated on the following criteria, that is, rated ○ when OD was 1.4 or more, rated Δ when from 1.2 to less than 1.4, or rated X when less than 1.2. The results are shown in Table 1.

<Evaluation of Light Fastness>

The coated material having an image density of 1.0 used for the evaluation of hue was irradiated with xenon light (99,000 lux.; in the presence of a TAC filter) for 35 days by using a fade meter and the color density before and after the xenon irradiation was measured using a reflection densitometer. Pigment Dispersions 1 to 10 and Comparative Pigment Dispersions 1 and 2 were evaluated and rated ○ when the colorant residual ratio [(density after irradiation/density before irradiation)×100%] was 80% or more, rated Δ when 60% or more, or rated X when less than 60%. The results are shown in Table 1.

<Evaluation of Ozone Gas Fastness>

The coated material having an image density of 1.0 used for the evaluation of hue was prepared and exposed for 28 days under the conditions of an ozone concentration of 5.0 ppm, 25° C. and a humidity of 50%, and the color density before and after the ozone gas exposure was measured using a reflection densitometer. Pigment Dispersions 1 to 10 and Comparative Pigment Dispersions 1 and 2 were evaluated and rated ○ when the colorant residual ratio [(density after irradiation/density before irradiation)×100%] was 80% or more, rated Δ when 70% or more, or rated X when less than 70%. The results are shown in Table 1.

As seen from these results, the pigment dispersion using the azo pigment composition of the present invention is easily dispersible and ensures good stability of the pigment dispersion. Furthermore, the coloring composition containing the pigment dispersion of the present invention is verified to give excellent hue as yellow and high tinctorial strength and be excellent also in the light fastness and ozone gas resistance.

Accordingly, the pigment-dispersed coloring composition containing the azo pigment composition of the present invention can be suitably used, for example, in an ink for printing such as inkjet recording, a color toner for electrophotography, a color filter for a display such as LCD and PDP or an imaging device such as CCD, a coating material, and a colored plastic.

Industrial Applicability

According to the present invention, an azo pigment composition excellent in the coloristic characteristics such as hue and tinctorial strength and also excellent in the dispersibility and dispersion stability is provided. By dispersing the pigment of the present invention in various mediums, a pigment dispersion excellent in coloristic characteristics, dispersibility and dispersion stability is obtained. The pigment dispersion can be used as a coloring material with excellent light fastness, for example, in an ink for printing such as inkjet recording, a color toner for electrophotography, a color filter for a display such as LCD and PDP or an imaging device such as CCD, a coating material, and a colored plastic.

While the invention has been described in detail and with reference to specific embodiments thereof, it will be apparent to one skilled in the art that various changes and modifications can be made therein without departing from the spirit and scope thereof.

TABLE 1

| | Coloring Agent Pigment Composition | Volume Average Particle Diameter | Dispersibility | Dispersion Stability | Hue | Tinctorial Strength | Light Fastness | Ozone Gas Fastness |
|---|---|---|---|---|---|---|---|---|
| Example 11 | α-type crystal morphology | 67 nm | ○ | ○ | ○ | ◎ | ○ | ○ |
| Example 12 | α-type/β-type = 9/1 | 64 nm | ○ | ○ | ◎ | ◎ | ○ | ○ |
| Example 13 | α-type/β-type = 8/2 | 68 nm | ○ | ○ | ◎ | ◎ | ○ | ○ |
| Example 14 | α-type/β-type = 6/4 | 67 nm | ○ | ○ | ○ | ○ | ○ | ○ |
| Example 15 | α-type/β-type = 5/5 | 70 nm | ○ | ○ | ○ | ○ | ○ | ○ |
| Example 16 | α-type/γ-type = 9/1 | 65 nm | ○ | ○ | ◎ | ◎ | ○ | ○ |
| Example 17 | α-type/γ-type = 8/2 | 66 nm | ○ | ○ | ◎ | ◎ | ○ | ○ |
| Example 18 | α-type/γ-type = 6/4 | 68 nm | ○ | ○ | ○ | ○ | ○ | ○ |
| Example 19 | α-type/γ-type = 5/5 | 72 nm | ○ | ○ | ○ | ○ | ○ | ○ |
| Example 20 | α,β mixed = about 9/1 | 60 nm | ○ | ○ | ◎ | ◎ | ○ | ○ |
| Comparative Example 1 | PY-74 | 50 nm | ○ | ○ | ○ | ○ | X | Δ |
| Comparative Example 2 | PY-155 | 45 nm | ○ | ○ | X | X | Δ | Δ |
| Comparative Example 3 | DYE-1 | fine particle dispersion was not formed | dissolved | — | — | — | — | — |

This application is based on Japanese Patent Application (Japanese Patent Application No. 2008-58711) filed on Mar. 7, 2008, Japanese Patent Application (Japanese Patent Application No. 2008-169182) filed on Jun. 27, 2008 and Japanese Patent Application (Japanese Patent Application No. 2008-251879) filed on Sep. 29, 2008, the contents of which are incorporated herein by way of reference.

The invention claimed is:

1. An azo pigment composition comprising at least one kind of an azo pigment represented by formula (1) having characteristic X-ray diffraction peaks at Bragg angles (2θ±0.2°) of 7.6°, 25.6° and 27.7° in the CuKα characteristic X-ray diffraction or a tautomer thereof:

Formula (I):

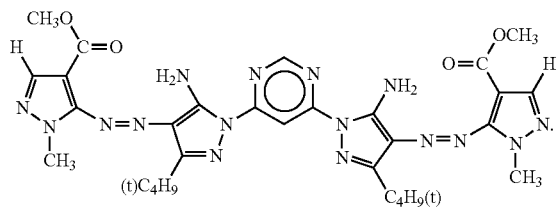

2. The azo pigment composition according to claim 1, wherein said composition further comprises at least from 0 to 50 mass % of an azo pigment represented by formula (1) with a crystal morphology having characteristic X-ray diffraction peaks at Bragg angles (2θ±0.2°) of 7.0°, 26.4° and 27.3° in the CuKα characteristic X-ray diffraction or a tautomer thereof.

3. The azo pigment composition according to claim 2, wherein the azo pigment represented by formula (1) with a crystal morphology having characteristic X-ray diffraction peaks at Bragg angles (2θ±0.2°) of 7.0°, 26.4° and 27.3° in the CuKα characteristic X-ray diffraction or a tautomer thereof is contained in an amount of at least from 0 to 20 mass %.

4. The azo pigment composition according to claim 2, wherein the azo pigment represented by formula (1) with a crystal morphology having characteristic X-ray diffraction peaks at Bragg angles (2θ±0.2°) of 7.0°, 26.4° and 27.3° in the CuKα characteristic X-ray diffraction or a tautomer thereof is contained in an amount of at least from 0 to 10 mass %.

5. The azo pigment composition according claim 1, wherein said composition further comprises at least from 0 to 50 mass % of an azo pigment represented by formula (1) with a crystal morphology having characteristic X-ray diffraction peaks at Bragg angles (2θ±0.2°) of 6.4°, 26.4° and 27.2° in the CuKα characteristic X-ray diffraction or a tautomer thereof.

6. The azo pigment composition according to claim 5, wherein the azo pigment represented by formula (1) with a crystal morphology having characteristic X-ray diffraction peaks at Bragg angles (2θ±0.2°) of 6.4°, 26.4° and 27.2° in the CuKα characteristic X-ray diffraction or a tautomer thereof is contained in an amount of at least from 0 to 20 mass %.

7. The azo pigment composition according to claim 5, wherein the azo pigment represented by formula (1) with a crystal morphology having characteristic X-ray diffraction peaks at Bragg angles (2θ±0.2°) of 6.4°, 26.4° and 27.2° in the CuKα characteristic X-ray diffraction or a tautomer thereof is contained in an amount of at least from 0 to 10 mass %.

8. A process for producing an azo pigment composition comprising at least one kind of an azo pigment represented by the following formula (1) or a tautomer thereof, comprising a step of performing an azo coupling reaction between a diazonium salt derived from a heterocyclic amine represented by the following formula (2) and a compound represented by the following formula (3):

Formula (2):

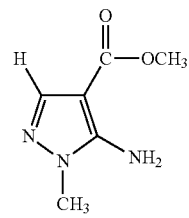

Formula (3):

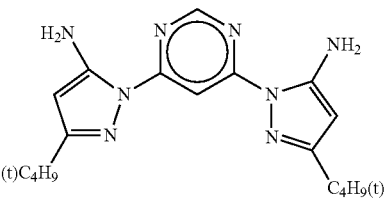

Formula (1):

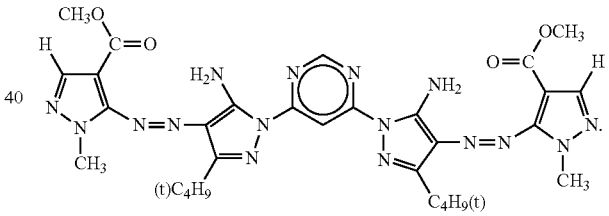

9. The production process according to claim 8, which further comprises a step of performing a post-treatment.

10. An azo pigment composition produced by the production process according to claim 8.

11. A dispersion comprising the azo pigment composition according to claim 1.

12. The pigment dispersion according to claim 11, wherein the volume average particle diameter is from 0.01 to 0.25 μm.

13. A coloring composition comprising the azo pigment composition according to claim 1 as a coloring agent.

14. An ink for inkjet recording, comprising the azo pigment composition according to claim 1 as a coloring agent.

* * * * *